(12) United States Patent
Holland

(10) Patent No.: US 9,585,307 B2
(45) Date of Patent: Mar. 7, 2017

(54) OPTICAL REAL-TIME SOIL SENSOR AND AUTO-CALIBRATION METHODS

(71) Applicant: Kyle H. Holland, Lincoln, NE (US)

(72) Inventor: Kyle H. Holland, Lincoln, NE (US)

( * ) Notice: Subject to any disclaimer, the term of this patent is extended or adjusted under 35 U.S.C. 154(b) by 324 days.

(21) Appl. No.: 14/305,207

(22) Filed: Jun. 16, 2014

(65) Prior Publication Data

US 2014/0358381 A1 Dec. 4, 2014

Related U.S. Application Data

(60) Continuation-in-part of application No. 13/901,221, filed on May 23, 2013, now Pat. No. 8,755,049, which is a division of application No. 12/914,415, filed on Oct. 28, 2010, now Pat. No. 8,451,449, application No. 14/305,207, which is a continuation-in-part of application No. 13/248,523, filed on Sep. 29, 2011, now Pat. No. 8,816,262, which is a continuation-in-part of application No. 12/815,721, filed on Jun. 15, 2010, now Pat. No. 8,558,157, which is a continuation of application No. 12/167,706, filed on Jul. 3, 2008, now Pat. No. 7,723,660.

(60) Provisional application No. 61/256,748, filed on Oct. 30, 2009, provisional application No. 60/598,330, filed on Jul. 3, 2007.

(51) Int. Cl.
| | |
|---|---|
| G01N 21/55 | (2014.01) |
| A01C 21/00 | (2006.01) |
| G01F 1/00 | (2006.01) |
| A01B 79/00 | (2006.01) |
| G01N 21/31 | (2006.01) |

(52) U.S. Cl.
CPC .......... *A01C 21/007* (2013.01); *A01B 79/005* (2013.01); *G01F 1/00* (2013.01); *G01N 21/31* (2013.01); *G01N 21/55* (2013.01); *G01N 2201/062* (2013.01); *Y02P 60/215* (2015.11)

(58) Field of Classification Search
CPC ................. A01C 21/007; G01N 21/55; G01N 2201/062; G01F 1/00; A01B 79/005; Y02P 60/215
USPC ........................ 250/206.1; 382/110; 702/2, 5
See application file for complete search history.

(56) References Cited

U.S. PATENT DOCUMENTS

| | | |
|---|---|---|
| 3,443,072 A | 5/1969 | Gibbs |
| 3,910,701 A | 10/1975 | Hendersen et al. |
| 4,055,768 A | 10/1977 | Bromberg |

(Continued)

OTHER PUBLICATIONS

Aronson, Milton H., "Low-Level Measurements-8 Lock-in and Carrier Amplifiers", Measurements and Data Corporation, pp. C1-C15, 1977.

(Continued)

*Primary Examiner* — Seung C Sohn
(74) *Attorney, Agent, or Firm* — McKee Voorhees and Sease PLC

(57) ABSTRACT

A method for application of an agricultural product to a field, the method includes acquiring real-time sampled data using real-time agricultural sensors, wherein the real-time agricultural sensors include a soil sensor, auto-calibrating the real-time agricultural sensors using statistical characteristics of the real-time sampled data to determine an application rate, and applying the agricultural product to the field based on the application rate.

27 Claims, 20 Drawing Sheets

(56) References Cited

U.S. PATENT DOCUMENTS

| | | | |
|---|---|---|---|
| 4,369,886 | A | 1/1983 | Lane et al. |
| 4,518,253 | A | 5/1985 | Takahashi |
| 4,628,454 | A | 12/1986 | Ito |
| 4,630,773 | A | 12/1986 | Ortlip |
| 4,926,170 | A | 5/1990 | Beggs et al. |
| 4,986,665 | A | 1/1991 | Yamanishi et al. |
| 5,025,150 | A | 6/1991 | Oldham et al. |
| 5,038,040 | A | 8/1991 | Funk et al. |
| 5,044,756 | A | 9/1991 | Gaultney et al. |
| 5,144,767 | A | 9/1992 | McCloy et al. |
| 5,220,876 | A | 6/1993 | Monson et al. |
| 5,296,702 | A | 3/1994 | Beck et al. |
| 5,355,815 | A | 10/1994 | Monson |
| 5,389,781 | A | 2/1995 | Beck |
| 5,585,626 | A | 12/1996 | Beck et al. |
| 5,763,873 | A | 6/1998 | Beck et al. |
| 5,789,741 | A | 8/1998 | Kinter |
| 5,809,440 | A | 9/1998 | Beck et al. |
| 5,833,144 | A | 11/1998 | Kinter |
| 5,837,997 | A | 11/1998 | Beck |
| 6,160,902 | A | 12/2000 | Dickson et al. |
| 6,366,681 | B1 * | 4/2002 | Hutchins ............ G06K 9/0063 382/110 |
| 6,393,927 | B1 | 5/2002 | Biggs |
| 6,529,615 | B2 | 3/2003 | Hendrickson et al. |
| 6,570,999 | B1 | 5/2003 | Monson |
| 6,596,996 | B1 | 7/2003 | Stone et al. |
| 6,601,341 | B2 | 8/2003 | Raun et al. |
| 6,889,620 | B2 | 5/2005 | Fraisse et al. |
| 6,937,939 | B1 | 8/2005 | Shibusawa et al. |
| 6,963,881 | B2 | 11/2005 | Pickett et al. |
| 6,999,877 | B1 | 2/2006 | Dyer et al. |
| 7,047,133 | B1 | 5/2006 | Dyer et al. |
| 7,049,597 | B2 | 5/2006 | Bodkin |
| 7,058,197 | B1 | 6/2006 | McGuire et al. |
| 7,171,912 | B2 | 2/2007 | Fraisse et al. |
| 7,188,450 | B2 | 3/2007 | Raun et al. |
| 7,723,660 | B2 | 5/2010 | Holland |
| 7,841,982 | B2 | 11/2010 | Johnson et al. |
| 8,135,178 | B2 | 3/2012 | Hendrickson et al. |
| 9,075,698 | B2 * | 7/2015 | Stachon ............ A01G 7/00 |
| 2001/0036295 | A1 | 11/2001 | Hendrickson et al. |
| 2002/0024665 | A1 | 2/2002 | Masten |
| 2002/0039186 | A1 | 4/2002 | Rosenberg |
| 2002/0131046 | A1 | 9/2002 | Christy et al. |
| 2004/0119020 | A1 | 6/2004 | Bodkin |
| 2006/0158652 | A1 | 7/2006 | Rooney et al. |

OTHER PUBLICATIONS

Burr-Brown, Applications Handbook. OPT201 Photodiode amplfier rejects ambient light. 1994. AB-061, p. 379.

Gage, S. Evans et al., Optoelectronics Applications Manual, 1977. McGraw-Hill Book Co.

Haggar, R.J. et al., "A Prototype Hand-Held Patch Sprayer for Killing Weeds, Activated by Spectral Difference in Crop/Weed Canopies", Agricultural Research Counsel, Nov. 15, 1982, pp. 349-358.

Haggar, R.J. et al., "Measuring Spectral Differences in Vegetation Canopies by a Reflectance Ratio Meter", Weed Research, 1984 vol. 24, pp. 59-65.

Hooper, A. W. et al., "A Photoelectric Sensor for Distinguishing between Plant Material and Soil" J. Agric. Engng. Res. (1976) 21, pp. 145-155.

Hyder, Dave, "Infrared Sensing and Data Transmission Fundamentals", Industrial Control Applications, Mar. 1991, DL412/D, AN1016, pp. 367-372.

Knipling, E.B., "Physical and Physiological Basis for the Visible and Near-Infrared Radiation from Vegetation", American Elsevier Publishing Company, Inc. 1970, pp. 155-159.

McAbe, D., "An Eye on Nitrogen", Precision AG, Mar. 2004, pp. 21-23.

McAbe, D., "Seeing the Light of Nitrogen", Nebraska Farmer, Feb. 1996, pp. 14, 15 and 20.

Motorola "Linear/Interface Devices", MC3346 and MC3373 Datasheets, 1988, pp. 9-42 to 9-46.

Palmer, J. et al., "Automatic Control of Sugar Beet Singling and Thinning by Means of an On-line Digital Computer", J. Agric. Eng. Res., (1971) vol. 16 (2), pp. 107-125.

Ritchie, J.C. et al., "Airborne laser measurements of rangeland canopy cover and distribution", J. Range Manage, Mar. 1992, 45:189-193.

Rsichenberger, Larry, "Tools With Eyes", Farm Journal, Mar. 1989, pp. 16-18.

Searcy, S. W. et al., "Measurement of Agricultural Field Location Using Microwave Frequency Triangulation" Computers and Electronics in Agriculture (1990), vol. 4, pp. 209-233.

Stafford, J. V. et al., "A Portable Infra-red Moisture Meter for Agricultural and Food Materials: Part 1, Instrument Development", J. Agric. Eng. Res. (1989), 43:45-46.

Stone, Marvin L. et al., Application of J1939 Networks in Agricultural Equipment, Oklahoma State University Dearborn Group, Stillwater, Oklahoma Farmington Hills, Michigan, http://biosystems.okstate.edu/home/mstone/ag. J1939.htm retrieved from the internet Dec. 13, 2010.

Thompson, J.F. et al., "Potential for Automatic Weed Detection and Selective Herbicide Application", Crop Protection (1991), vol. 10, p. 254-259.

Girma, Kefyalew et al., "Nitrogen Accumulation in Shoots as a Function of Growth Stage of Corn and Winter Wheat", Journal of Plant Nutrition, Dec. 1, 2010, 34:2, 165-182.

Hodgen, P. J. et al., "Relationship Between Response Indices Measured In-Season and at Harvest in Winter Wheat", Journal of Plant Nutrition, 2005, 28: 221-235.

Holland, K. H. et al., "Derivation of a Variable Rate Nitrogen Application Model for In-Season Fertilization of Corn", Agronomy Journal, 2010, vol. 102, Issue 5, pp. 1415-1424.

Raun, William R. et al., "Independence of yield potential and crop nitrogen response" Precision Agri., Oct. 2, 2010, DOI 10,1007/s11119-010-9196-z; Springer Science+Business Media, LLC, 2010.

Raun, William R. et al., "Chapter 10—Temporally and Spatially Dependent Nitrogen Management for Diverse Environments" c10.indd, Jan. 22, 2009, pp. 203-214.

Shanahan, J.F. et al., "Responsive in-season nitrogen management for cereals", Computers and Electronics in Agriculture 61 (2008) pp. 51-62.

* cited by examiner

OPTICAL REAL-TIME SOIL SENSOR AND AUTO-CALIBRATION METHODS

CROSS-REFERENCE TO RELATED APPLICATIONS

This application is a Continuation-in-Part of Ser. No. 13/901,221 now U.S. Pat. No. 8,755,049 issued Jun. 17, 2014, filed May 23, 2013, which is a Divisional Application of U.S. Ser. No. 12/914,415 filed Oct. 28, 2010, now U.S. Pat. No. 8,451,449 issued May 28, 2013, which claims priority under 35 U.S.C. §119 to provisional application Ser. No. 61/256,748 filed Oct. 30, 2009, all of which are herein incorporated by reference in their entirety.

This application is also a Continuation-in-Part of Ser. No. 13/248,523; filed Sep. 29, 2011 now U.S. Pat. No. 8,816,262 issued Aug. 26, 2014, which is a Continuation-in-Part Application of U.S. Ser. No. 12/815,721; filed on Jun. 15, 2010 now U.S. Pat. No. 8,558,157 issued Oct. 15, 2013, which is a Continuation Application of U.S. Ser. No. 12/167,706 filed Jul. 3, 2008, now U.S. Pat. No. 7,723,660 issued May 25, 2010, which claimed priority to U.S. Ser. No. 60/958,330 filed on Jul. 3, 2007, all of which are hereby incorporated by reference in their entirety.

BACKGROUND OF THE INVENTION

Field of the Invention

The present invention relates to variable rate material management for agricultural landscapes. More particularly, but not exclusively, the present invention relates to auto-calibration of real-time sensors used in the application of agricultural products such as agrochemicals and seeds, including soil content sensors.

Problems in the Art

Various methodologies are available to crop producers which allow them to apply agrochemicals. Some methodologies use real-time active crop or soil sensors for variable rate control of agrochemicals and seed rate. Yet problems remain in providing effective calibration of these sensors.

Another problem relates to fact that organic matter content of a soil is a significant variable in modern soil management and relates to a soil's adsorption of pesticides, its water holding capacity, and its yield potential are often related to its organic matter content. By sensing a landscape's organic matter content in real-time, the potential of applying agricultural products without the use of preprocessed maps will allow producers to optimize their use as well as maximizing profitability.

Conventional agricultural equipment is designed to apply chemicals and plant crops at uniform rates within a field, regardless of changes in soil type or organic matter content. This can result in an over application of chemicals in some areas of the field, an under application in other areas, overplanting in some areas and under planting in others. It would therefore be desirable to provide a prescription application system which would rapidly and accurately adjust chemical and seeding rates by sensing variations in soil type and organic matter as equipment traverses a field. There is thus a need for an apparatus that will sense the organic content of soil as chemicals are being applied or crops planted so that the application of the chemicals or the seeding can be adjusted based upon the sensed organic matter content of the particular area of the field to be treated or planted. In the past couple decades, there has been interest in developing agricultural equipment capable of sensing soil organic matter content and adjusting the corresponding application rate of herbicides, seeds or fertilizer as the equipment moves across the field. Such sensing systems require knowledge of the mathematical relationship between organic matter content and soil color. In general, progress in developing such sensor systems has proven to be unsatisfactory because the developers have attempted to develop universal relationships between organic matter content and sensor output. The problem with this approach is that it is known that different soil associations can have different relationships between organic matter content and soil color. Another problem faced in developing an accurate real-time soil organic matter sensor is that the scene, i.e., particular area of the soil that is being observed by the sensor, must have a generally uniform surface. These sensors typically work by reflecting light off the scene. If the surface of the scene is not uniform, the reflectance will vary in response to surface roughness changes yielding erroneous results. Variations in the surface of the scene can be caused by differences in soil texture, size of the soil aggregates, moisture content, etc. Ambient light can also adversely affect the accuracy of such sensors by introducing a second, variable source of light which is also reflected from the scene and picked up by the sensor.

What is needed are systems and methods which are simple and convenient for agricultural producers to use while still resulting in application of agrochemicals and agricultural materials in acceptable and desirable manners.

BRIEF SUMMARY OF THE INVENTION

It is an object, feature, or advantage of the present invention to provide an apparatus for sensing the organic matter content of soil on a real-time basis.

It is another object, feature, or advantage of the present invention to provide an apparatus for sensing the organic matter content of soil that auto calibrates itself while being pulled through the field.

It is a further object, feature, or advantage of the present invention to provide a means to rebuild/service the wear surfaces of the apparatus in the field.

It is a still further object, feature, or advantage of the present invention to provide an apparatus for sensing the organic matter content of soil that is immune to influence of ambient light.

It is another object, feature, or advantage of the present invention to provide a soil sensor that reduces problems caused by variations in soil moisture and surface roughness.

It is a further object, feature, or advantage of the present invention to provide for methods and systems for application of agrochemicals and agricultural materials which use real-time sensors to assist in the application of the agrochemicals and agricultural materials.

It is a still further object, feature, or advantage of the present invention to provide for methods and systems for application of agrochemicals which do not require the use of crop reference strips or regions for calibration purposes.

Another object, feature, or advantage of the present invention is to provide for methods and systems for applications of agrochemicals which allow for users to select the methodology or algorithms to be used.

Yet another object, feature, or advantage of the present invention is to allow a crop producer to variably control rate of application of agrochemicals without driving through at least a portion of the field for calibration purposes.

A still further object, feature, or advantage of the present invention is to use adaptive algorithms for variably controlling the rate of application of agrochemicals within a field.

A further object, feature, or advantage of the present invention is to provide for variable rate control which does not require the use of GPS data.

A still further object, feature, or advantage of the present invention is to provide for variable rate control methodologies which may be used with remote sensing as well as real-time active sensors.

A still further object, feature, or advantage of the present invention is to provide for variable rate control methodologies which may be used with electromagnetic, conductivity, chemical, tilt, topology and force real-time sensors.

A still further object, feature, or advantage of the present invention is to provide for best management practice implementation based on data produced by real-time sensor and variable rate control methodologies which may be used with electromagnetic, optical, conductivity, chemical, tilt, topology and force real-time sensors.

A still further object, feature, or advantage of the present invention is to provide for plant selection via data collected by sensors (electromagnetic, optical, conductivity, chemical, tilt, topology and force real-time sensors) for the purpose of selecting plants based on genetic trait or vigor characteristic selection. Information can be processed either in real-time or post processed.

One or more of these and/or other objects, features, or advantages will become apparent from the specification and claims that follow. No single embodiment of the present invention need exhibit each or any of the objects, features, or advantages and different embodiments may have different objects, features, or advantages. The present invention is not to be limited by or to these objects, features, or advantages.

The apparatus preferably includes a member that prepares the surface of the soil scene immediately before it is observed by the sensor to provide a generally uniform surface, i.e., generally flat and smooth. One embodiment of the apparatus senses subsurface soil reflectance at depths typically ranging from 10 cm to 25 cm while another embodiment of the apparatus senses the freshly tilled surface remotely (non-contact) from a distance of 3 cm to 50 cm (or greater) distance from the soil surface. Further, the light source preferably comprises solid-state emitters that are arranged in proximity to a photodiode or array of photodiodes. The soil is sensed through a scratch resistant transparent material that is in contact with the soil surface in the case of the subsurface sensor or above the surface in the case of the noncontact embodiment. The apparatus also preferably includes a processor that processes the light sensed by the light sensor to determine the organic matter content of the soil at the soil scene. The processor in some embodiments uses an average organic matter content value determined by a soil sampling service provider and auto calibrates the sensor as it is pulled through the field. In other embodiments, the processor has data reflecting an experimentally determined characterization of the soil in the local geographic area where the soil being sensed is located. This data comprises a mathematical equation for different classes of soils, e.g., a linear regression equation for soils having a low sand content and a curvilinear regression equation for soils with a relatively higher sand content. Further, each such equation has parameters which are determined from the particular landscape where the apparatus is used. The processor uses the appropriate mathematical equation to solve for the organic matter content of the soil using the sensed reflected light as an input to the equation.

Conceptually, a system for close range remote sensing of soil color, including the soil itself, can be characterized as having four basic components—an illumination device, a scene, a sensor, and an algorithm processor. The illumination device is illustratively an active light source that illuminates the soil scene. The desired information is contained in the spectral variations of the electromagnetic energy emanating from the scene. The sensor collects the energy and measures its features. The processor will implement an auto calibration algorithm using a field or landscape's average organic matter content as a single input value or for initialization, or a deterministic algorithm which will make an appropriate estimation based on feature measurements provided by the output from the sensor. As will be discussed in more detail later, the apparatus of this invention senses the magnitude of light, illustratively provided from a solid state light source, that is, reflected from the scene and determines the organic matter content based on the magnitude of the reflected light.

The apparatus may be used for creating soil maps or for varying the application rate of an agricultural product or seed rate of a landscape. Typically, the apparatus will be interfaced to an agricultural controller that is used to collect and variably apply an agricultural product. Communication between apparatus and agricultural controller is performed via a serial communication bus.

According to one aspect, a sensor for measuring organic matter content of soil includes a replaceable wear surface, a corrosion resistant enclosure, and a light source for illuminating the soil with light. There is at least one photo detector to receive reflected light from the soil. There is also a scratch resistant optical window in contact with the soil, wherein the optical window allows light from the light source to illuminate the soil and the reflected light emanating from the soil to reach the at least one photo detector.

According to another aspect, a sensor for measuring organic matter content of soil includes a corrosion resistant enclosure, and a light source for illuminating the soil at a distance with light. There is at least one photo detector to receive reflected light from the soil. There is also a scratch resistant optical window wherein the optical window allows light from the light source to illuminate the soil and the reflected light emanating from the soil to reach the at least one photo detector.

According to another aspect, a method for measuring organic matter content of soil is provided. The method includes moving a sensor through a field. While moving the sensor through the field, the method includes illuminating the soil with light from a light source passing through an optical window of the sensor in contact with the soil. While moving the sensor through the field, the method includes receiving reflected light through the optical window of the sensor at least one photodetector. The method also includes processing a signal from each of the at least one photodetector to determine the organic matter content of the soil.

According to another aspect, a system for use in measuring organic matter content of soil is provided. The system includes a soil sensor. The soil sensor includes: (a) a replaceable wear surface, (b) a corrosion resistant enclosure, (c) a light source for illuminating the soil with light, (d) at least one photo detector to receive reflected light from the soil, and (e) a scratch resistant optical window in contact with the soil, wherein the optical window allows light from the light source to illuminate the soil and the reflected light emanating from the soil to reach the at least one photo detector. The system further includes a phase detection circuit operatively connected to the at least one photo detector. The system further includes an analog-to-digital converter operatively connected to the phase detection circuit. The system also includes an intelligent control operatively connected to the analog-to-digital converter.

According to another aspect, a system for use in measuring organic matter content of soil is provided. The system includes a soil sensor. The soil sensor includes: (a) a corrosion resistant enclosure, (b) a light source for illuminating the soil with light, (c) at least one photo detector to receive reflected light from the soil, and (d) a scratch resistant optical window, wherein the optical window allows light from the light source to illuminate the soil and the reflected light emanating from the soil to reach the at least one photo detector. The system further includes a phase detection circuit operatively connected to the at least one photo detector. The system further includes an analog-to-digital converter operatively connected to the phase detection circuit. The system also includes an intelligent control operatively connected to the analog-to-digital converter.

According to another aspect, a method for measuring organic matter content of soil is provided. The method includes moving a sensor through a field. While moving the sensor through the field, the method provides for illuminating the soil with light from a light source passing through an optical window of the sensor in contact with the soil. While moving the sensor through the field, the method provides for receiving reflected light through the optical window of the sensor at least one photodetector. The method further provides for determining reflectance at a plurality of different wavelengths for the light, normalizing the reflectance to provide a normalized reflectance to reduce sensitivity to variations in water content of the soil, and determining the organic matter content of the soil using the normalized reflectance.

According to another aspect, a method for determining organic matter content of soil is provided. The method includes moving a sensor through a field, while moving the sensor through the field, illuminating the soil with light from a light source, while moving the sensor through the field, receiving reflected light, determining reflectance associated with the reflected light, and determining the organic matter content of the soil using the reflectance through use of an auto-calibrated algorithm.

Various methods are provided for practicing sensor-based precision farming techniques pertaining to the application of materials such as seeds, fertilizer, pesticides, herbicides or other agricultural substances. A highly fertilized reference area (or controlled agrochemical region whether it be treated with a high or low dose of material) is not required to calibrate the sensing system for application of an agrochemical and thereby eliminates the extra management steps and overhead required by the producer to create, locate and maintain these portions of a field. Additionally, the methodologies disclosed hereafter are not limited to real-time active sensors but may also be applied to other remote sensing technologies such as aerial and satellite imaging.

According to one aspect, a method for application of an agricultural product to a field is provided. The method includes acquiring real-time sampled data using real-time agricultural sensors, auto-calibrating the real-time agricultural sensors using statistical characteristics of the real-time sampled data to determine an application rate, and applying the agricultural product to the field based on the application rate. The step of auto-calibrating can be performed in various ways depending upon the type of agricultural product, the data available from the agricultural sensors or otherwise, or otherwise.

According to another aspect, an apparatus for application of an agricultural product to a field is provided. The apparatus includes one or more real-time agricultural sensors, and a control unit in operative communication with the plurality of real-time agricultural sensors, the control unit configured to perform steps of (a) acquiring real-time sampled data using the real-time agricultural sensors, (b) auto-calibrating the real-time agricultural sensors using statistical characteristics of the real-time sampled data to determine an application rate, and (c) applying the agricultural product to the field based on the application rate.

According to another aspect, a method is provided. The method includes acquiring real-time sample data with agriculture sensors, auto-calibrating the agriculture sensors using an auto-calibrate engine to determine an application rate, applying agricultural product at the application rate; maintaining location data associated with the real-time sample data and the application rate data and identifying locations in which plants exhibit characteristics of interest after application of the agricultural product.

According to another aspect, a method provides for acquiring sample data with agriculture sensors traveling through a field, the sample data having location data associated therewith and analyzing the sample data using statistical characteristics to determine plants within the field having characteristics of interest. The sample data may be analyzed with a histogram method. The plants of interest may be associated with vegetation index values of interest.

According to another aspect, a method for application of an agricultural product to a field is provided. The method includes acquiring real-time sampled data using real-time agricultural sensors, wherein the real-time agricultural sensors include a soil sensor, auto-calibrating the real-time agricultural sensors using statistical characteristics of the real-time sampled data to determine an application rate, and applying the agricultural product to the field based on the application rate.

According to another aspect, an apparatus for application of an agricultural product to a field is provided. The apparatus includes a plurality of real-time agricultural sensors and a control unit in operative communication with the plurality of real-time agricultural sensors, the control unit configured to perform steps of (a) acquiring real-time sampled data using the real-time agricultural sensors, (b) auto-calibrating the real-time agricultural sensors using statistical characteristics of the real-time sampled data to determine an application rate, and (c) applying the agricultural product to the field based on the application rate. At least one of the plurality of real-time agricultural sensors is a soil sensor.

BRIEF DESCRIPTION OF THE DRAWINGS

Additional features and advantages of the invention will become apparent to those skilled in the art upon consideration of the following detailed description of typical embodiments, exemplifying the best modes of carrying out the invention as presently perceived. The detailed description particularly refers to the accompanying figures:

FIG. 10A illustrates sensor measurement. FIGS. 10B to 10E were generated from soil samples along the measurement transect. The soil sensor was calibrated to the field's average organic matter content. Note, NPK measurements roughly track sensor measurements whereas field elevation does not.

DETAILED DESCRIPTION

Chemical and physical properties vary from soil to soil and affect the reflectance and absorption characteristics of each soil. Color is an obvious soil property and can be used as an indirect measure of other soil characteristics. Soil is a heterogeneous substance and thus has a variety of different factors that affect reflectance. The reflectance of electromagnetic energy and the factors that attenuate the amplitude of the electromagnetic energy reflected from a soil surface must be considered in an appropriate sensor design. The factors affecting soil reflectance are texture, moisture content, surface roughness, iron oxide content, and organic matter content.

Variations in moisture content are much more severe at surface level than beneath the soil surface. At the surface level, moisture can vary exceedingly due to differential drying of the surface, residue cover, and changes in topography. Beneath the soil surface, however, moisture content is more uniform and at a level where a slight variance in moisture content might not significantly affect reflectance. Subsequently, the apparatus has been designed specifically to sense soil beneath the soil's surface or to sense a freshly worked soil surface at time of planting, tilling, seeding, etc. . . .

A major variable affecting soil reflectance is the surface roughness. The energy reflected from a soil surface is decreased by increased surface roughness. Surface roughness tends to be more of a problem at closer ranges due to a smaller sampling area. The rough surface diffuses light over a larger scene than is normally viewed by the sensor. Using a multiple wavelengths of light when sensing can minimize the effect of surface roughness for noncontact sensors such as disclosed as one embodiment.

Surface roughness is predominately determined by soil tillage practices. A minimum tillage practice tends to create a rougher surface than conventional tillage practice where larger soil aggregates are reduced in size by increased tillage processes. Thus, it is important to provide for some minimum amount of soil conditioning to produce a uniform, constant surface when attempting to determine the organic matter content of soil by light reflectance, regardless of any previous tillage of the soil.

Figure 1:
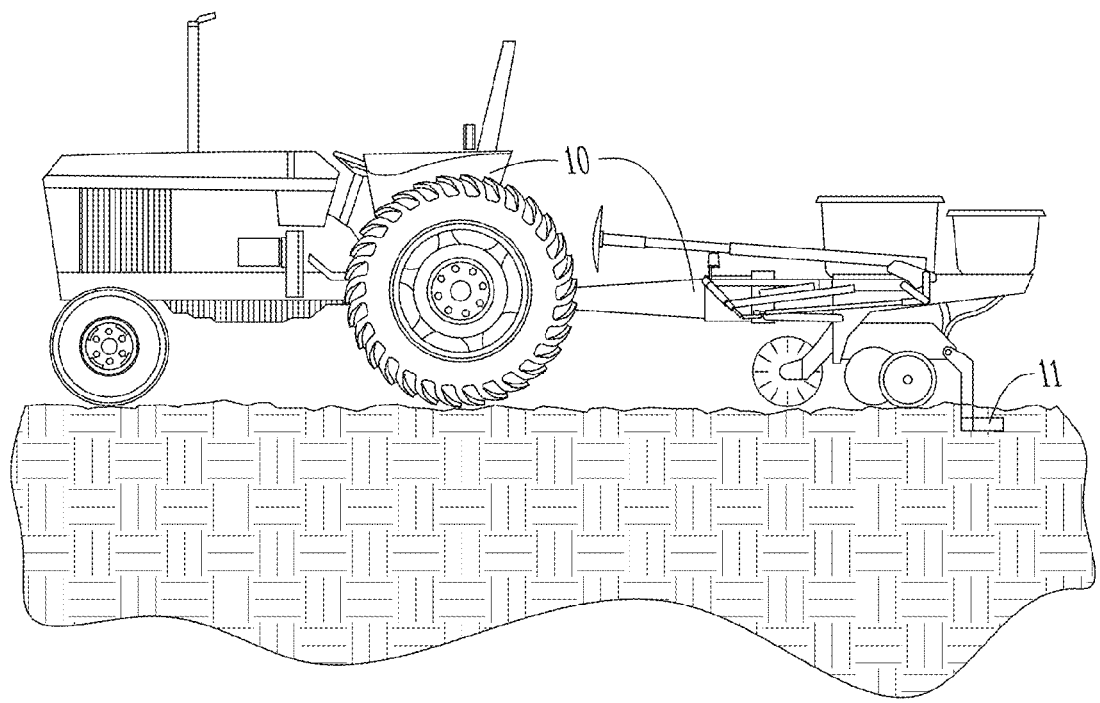
FIG. 1. Diagram of sensor pulled through field by tractor while mounted to agricultural implement.
Figure 2:
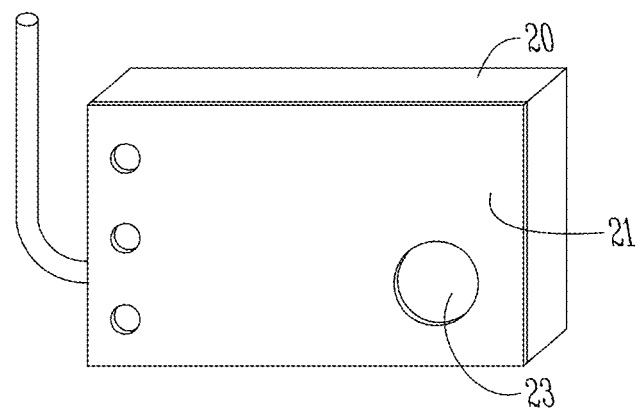
FIG. 2. Diagram of sensor enclosure having a replaceable wear plate.
Figure 3:
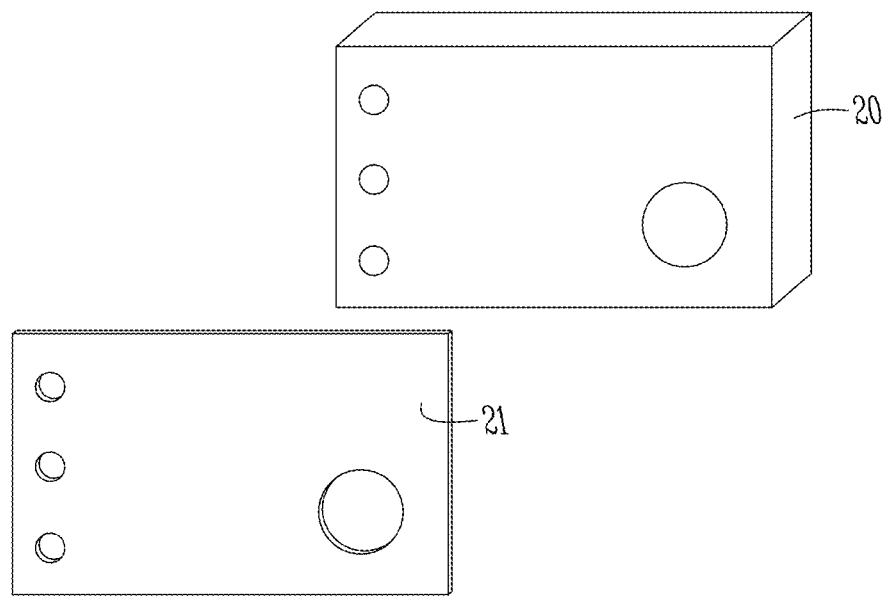
FIG. 3. Diagram of sensor with wear plate separated from corrosion resistant body.

In practice, the sensor apparatus 11 will be connected to a piece of agricultural equipment 10 and pulled through a field as shown in FIG. 1. The sensor 11 will be positioned by the operator so as to measure soil reflectance at a preferred depth of about 10 to 25 cm under the soil surface. FIG. 2 shows a diagram of the sensor enclosure. The sensor enclosure 20 will most preferably be made of a corrosion resistant metal (stainless steel, aluminum, etc.) or plastic material (teflon, pvc, polyethelene, etc.). The enclosure facilitates the protection of the electronic circuitry while providing optical emission and reception port 23 for the light source and the light detector components, respectively, of the sensor. A unique feature of the enclosure pertains to a field rebuildable wear surface also referred to as a field replaceable wear surface 21. The wear surface is intended to increase the longevity of the sensor enclosure by limiting abrasion to the enclosure. This wear surface is intended to be maintained by the operator on an annual basis. The material for this wear surface can be metal (steel, stainless steel, etc.) or plastic (Teflon, UHMW polyethelene, etc.) and can be fastened to the enclosure body 20 with adhesives and/or fastening hardware such as screws. FIG. 3 shows the enclosure with the wear surface 21 separated from enclosure 20. The optical port 23 in FIG. 2 is covered by a hard, transparent window. This window can be made of various types of optical materials to protect the emitter and detector electronics. The optical material should have a mohs hardness greater than 6. Materials meeting this hardness requirement include, but not limited, to quartz and sapphire. To those skilled in the art it should be readily apparent that the sensor optics can take on many forms.

Figure 8:
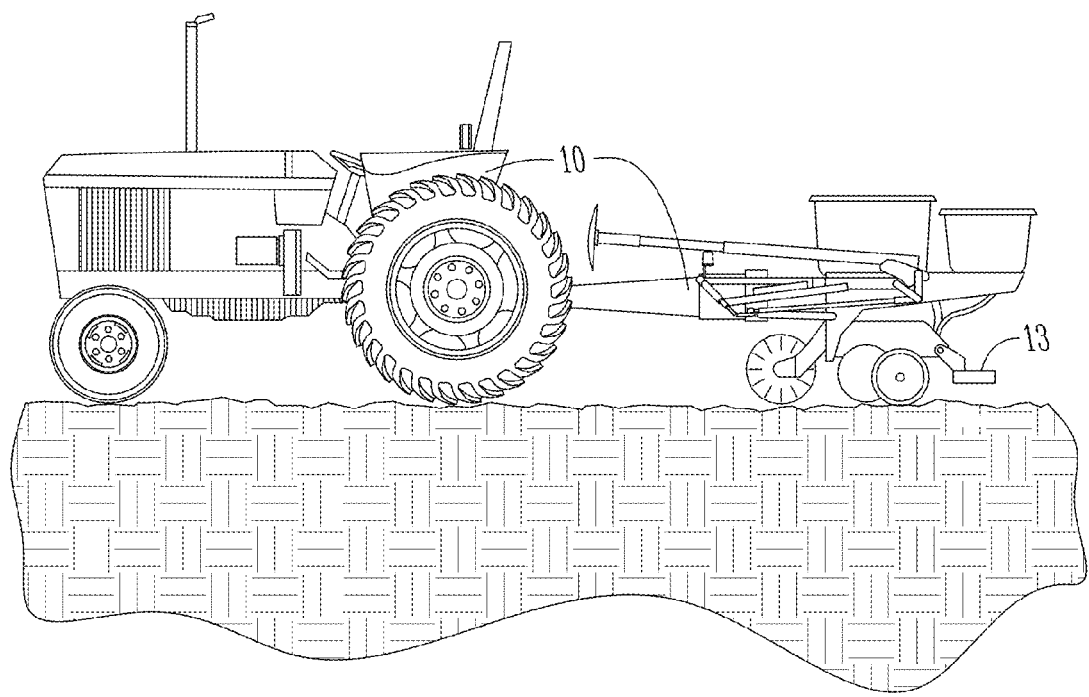
FIG. 8. Diagram of noncontact sensor 13 above the soil surface.

Additionally, the sensor apparatus 13 will be connected to a piece of agricultural equipment 10 and driven over a field as shown in FIG. 8. The sensor 13 will be positioned by the operator so as to measure soil reflectance of freshly worked soil at a preferred distance of about 3 to 50 cm above the soil surface. FIG. 2 shows a diagram of the sensor enclosure. The sensor enclosure 20 will most preferably be made of a corrosion resistant metal (stainless steel, aluminum, etc.) or plastic material (teflon, pvc, polyethelene, etc.). The enclosure facilitates the protection of the electronic circuitry while providing optical emission and reception port 23 for the light source and the light detector components, respectively, of the sensor. The optical port 23 in FIG. 2 is covered by a hard, transparent window. This window can be made of various types of optical materials to protect the emitter and detector electronics. The optical material should have a mohs hardness greater than 6. Materials meeting this hardness requirement include, but not limited, to quartz and sapphire. To those skilled in the art it should be readily apparent that the sensor optics can take on many forms. Plastics may be used but may be prone to scratching during cleaning. If plastic materials are used, the optical windows will be replaceable in the event of scratching or clouding from cleaning operations.

Figure 4:
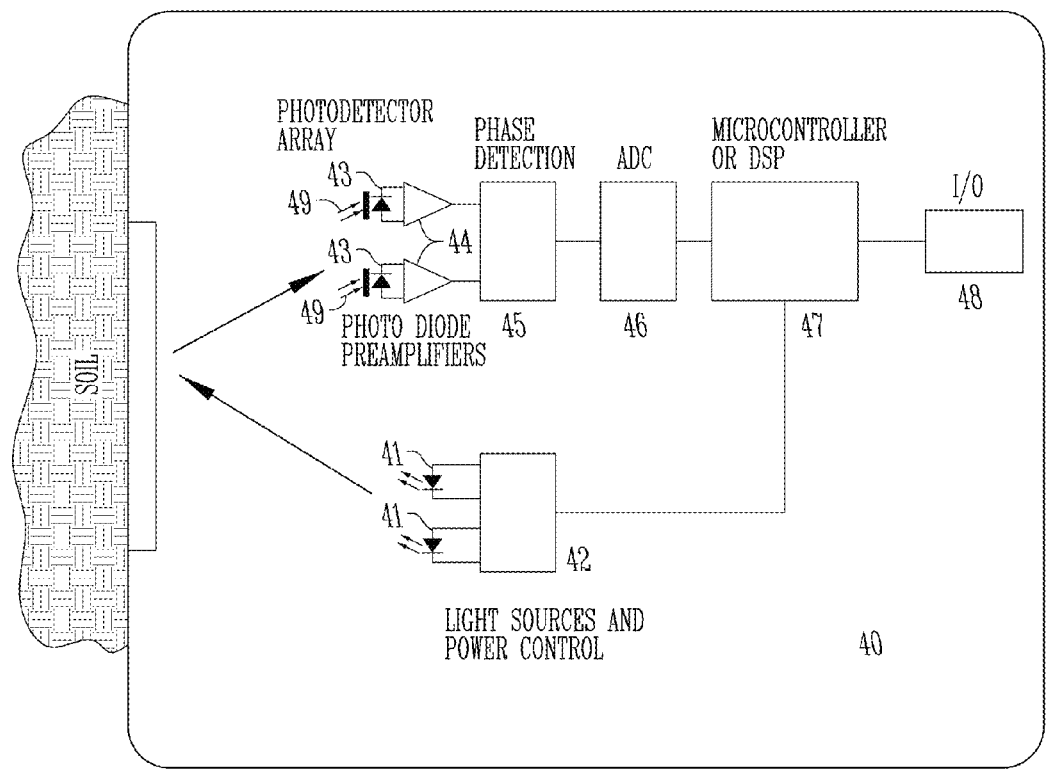
FIG. 4. Sensor electronics block diagram.

FIG. 4 shows a system diagram typical for the many embodiments of the invention. The sensor 40 is composed of optics to facilitate optical energy collimation and collection, a modulated light source 41 comprised of one or many banks of polychromatic LEDs and/or monochromatic LEDs or laser diodes (LD) with associated modulated driver and power control electronics 42, one or more photodetectors 43, high-speed preamplifier circuitry with ambient light cancellation 44, a phase sensitive signal conditioning 45 and data acquisition circuitry 46, and a microcontrol unit (MCU) or digital signal processor (DSP) 47 and an input/output interface 48 to communicate sensor data to an operator or controller. These system elements will be discussed in the following. Some embodiments will require spectral or specular band shaping/filtering. This function is performed using element 49.

The light source for the invention is most preferably composed of light emitting diodes or laser diodes. LEDs are convenient light sources for this type of invention for a number of reasons. First, LEDs are available in a number of colors useful for making soil reflectance measurements. LEDs are readily available in colors spanning from deep violet (395 nm) to near infrared (940 nm). Most recently, the UV LEDs have been developed in the 350 nm to 370 nm. These particular devices might be useful for stimulating fluorescence in soil. Another useful class of LEDs has been recently developed for the telecommunications industry. These devices have spectral emissions spanning from approximately 600 nm to 1550 nm. This range of devices is particularly useful for measuring water absorption bands in soil. Second, LEDs are extremely easy to use and can be modulated to megahertz frequencies. Relatively simple electronic driver circuits can be implemented and easily controlled by sensor controller electronics. Last, LEDs have long lifetimes and are rugged. The typical monochromatic LED will operate between 80,000 and 100,000 hours depending on the quiescent device power and operating temperature range.

Another useful type of LED is the phosphor coated LED. Phosphor coated LED's are convenient light sources for this type of invention for a number of reasons. First, white light emitting LED's are available that have spectral emission characteristics that are useful for making soil color measurements. These LED's can be constructed to have color temperatures that span from deep violet (400 nm) to near infrared (900 nm). Second, white light LED's using phosphor coatings over UV or blue LED emitters can have lifetimes of 40,000 to 80,000 hours.

Most white light emitting LED's in production today are based on an InGaN—GaN structure, and emit blue light of wavelengths between 450 nm-470 nm blue GaN. These GaN-based, InGaN-active-layer LED's are covered by a yellowish phosphor coating usually made of cerium-doped yttrium aluminum garnet (Ce3+:YAG) crystals which have been powdered and bound in a polymer or silicone adhesive. The LED chip emits blue light, part of which is efficiently converted to a broad spectrum centered at about 580 nm (yellow) by the Ce3+:YAG. The emission color of Ce3+: YAG emitters can be modified by substituting the cerium with other rare earth elements such as terbium and gadolinium and can even be further adjusted by substituting some or all of the aluminum in the YAG with gallium. Due to the spectral characteristics of the diode, the red and green colors of objects in its blue yellow light are not as vivid as in broad-spectrum light. Manufacturing variations and varying thicknesses in the phosphor make the LED's produce light with different color temperatures, from warm yellowish to cold bluish. Spectrum of a white LED clearly showing blue light which is directly emitted by the GaN-based LED (peak at about 465 nanometers) and the more broadband stokes shifted light emitted by the Ce3+:YAG phosphor which extends from around 500 to 700 nanometers. White LEDs can also be made by coating near ultraviolet emitting LEDs with a mixture of high efficiency europium based red and blue emitting phosphors plus green emitting copper and aluminum doped zinc sulfide (ZnS:Cu, Al). This is a method analogous to the way fluorescent lamps work. The spectrum of a white LED is easily modified to create other colors by modifying the elemental components in the phosphor coating. For example, an orange, broad-band LED can be created to emit longer wavelengths of light—higher intensities of red and NIR—by using a phosphor coating containing a mixture of gadolinium, aluminum, oxygen and cerium ($Gd_3Al_5O_{12}$:Ce) over a 470 nm LED die. It should be noted that there are numerous other methods, that one skilled in the art, can create different spectral outputs for LED devices (using green, yellow and red phosphor compounds) having the basic structure of the white phosphor LED.

Figure 7:
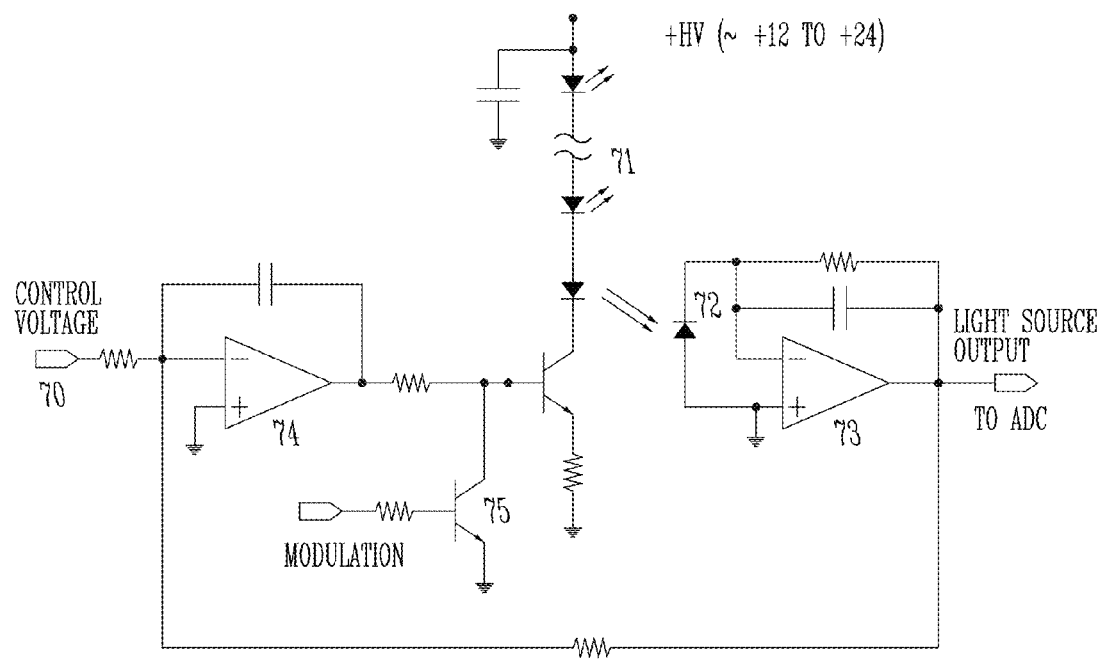
FIG. 7. Temperature compensation circuitry for LED output intensity control.

The output intensity of LEDs is very temperature dependent. Depending on the material type, an LEDs output can drift between 0.4%/C and 1%/C. A decrease in output intensity, even it is being monitored and corrected via calculation, can result in diminished signal to noise performance of the measurement. FIG. 7 shows schematically a circuit that provides active power control for the light source and an output intensity signal for monitoring and calibration. Control voltage 70 sets the output power of light source 71. Photodiode 72, an Infineon SFH203 (Munich, Germany), samples part of the output intensity of light source 71 and feeds this signal via amplifier 73 to servo amplifier 74. Modulation of the output signal is performed using transistor 75. Furthermore, the output of amplifier 73 can be utilized to monitor the light source intensity for purposes of calibration and diagnostics. The performance of this circuit has provided output intensity control of approximately 0.05%/C over the operating range of the invention. When a polychromatic source is utilized, a photodiode and amplifier are incorporated into the circuit so as to monitor the IR output of the light source. Suitable photodiodes in this case would be a SFH203FA for photodiode and a SFH203 for photodiode 72. Both diodes are manufactured by Infineon (Munich, Germany). Many techniques have been discussed in literature detailing methods on maintaining and stabilizing light sources for photometric type measurements including the method presented here.

The photodetectors used in the invention are most preferably silicon photodiodes however other detector technologies such as GaAsP, InGaAs, GaP, and the like, may be utilized as well. The choice in a particular photodetector is determined by the type of light source chosen for the sensor. Silicon detectors have a typical photosensitivity spanning from 200 nm (blue enhanced) to 1200 nm. When using narrow band light sources, no additional spectral filtering or band shaping is usually necessary. However, when using broadband light source like white LED's spectral filtering or band shaping is required. Band shaping of the detectors is performed using filtering materials such as colored filter glass, interference filters or dichroic filters. Additionally, some embodiments of the invention may utilize polarizing filters to minimize the impact specular reflectance on the measured signal so as to better measure diffuse reflectance from the soil.

As will be apparent to one skilled in the art, various combinations of the aforementioned filter techniques can be combined in order to band-shape the radiation impinging on the photodetector surface.

The output from the photodetector (or photodetector array) 43 in FIG. 4 is amplified using a transconductance amplifier with a feedback servo to cancel the effects of ambient light. The composite amplifier acts as an AC amplifier that allows only modulated reflectance signals resulting from the modulated light source to pass on to the later stages of the sensor's instrumentation. DC or slowly varying light signals are not amplified and are rejected by the sensor photodetector conditioning circuitry. This is important in situations where the sensor/soil interface may open and allow sunlight to reach the photodetector. In this situation, the influence of sunlight is rejected and amplifier circuitry does not saturate.

Referring once again to FIG. 4, the invention utilizes a phase sensitive detector circuit (PSD) 45 and analog-to-digital converter 46 (ADC) after each photodetector. The PSDs, also refer to as a lock-in amplifiers, are utilized by the invention to extract and further amplify the very small signal detected and amplified by the photodetector preamplifiers. PSDs are often used in applications where the signal to be measured is very small in amplitude and buried in noise. Detection is carried out synchronously with modulation of the light source. Phase sensitive detection is one of many types of band narrowing techniques that can be utilized to measure small signals. As will be apparent to those skilled in the art, other methods include the use of averaging techniques, discriminators and direct digital conversion/processing. With respect to direct digital conversion/processing, the phase sensitive acquisition component can be performed internally to a MCU or DSP by directly sampling the output of the photodiode amplifiers and performing the bandpass and PSD functions digitally. By performing these operations in the digital domain, the temperature drift of the phase detector, common to analog techniques, can be eliminated. The invention performs the synchronous modulation/demodulation at a carrier frequency of 10 kHz. It should be noted that the operation of the invention is not limited to this particular modulation rate and can operate at other modulation as well with as much effectiveness. Additionally, this rate can be increased or decreased as dictated by the application. The MCU or DSP samples the output of a PSD 45 utilizing ADC 46. The resolution of the ADC is most preferably greater than 12 bits. Each channel can sampled using a dedicated ADC or one ADC can be utilized to sample all channels via a multiplexer.

Once the detected optical signals are amplified, demodulated and quantified, the MCU or DSP 47 can calculate the soil's organic matter content based on the reflectance values sensed. It is important to minimize the influence of moisture on the reflectance signature of the soil. The invention accomplishes this by using normalizing, in particular, normalizing the reflectance at a particular wavelength with respect to slope of the soil reflectance curve. This is primarily accomplished using a difference of two or more wavelengths in the denominator of a ratio based expression. The equation utilized is shown below:

$$MCR1 = \frac{\rho_{\lambda 1}}{\rho_{\lambda 1} - \rho_{\lambda 2}}, \lambda 1 > \lambda 2$$

where MCR1 is the moisture compensated reflectance,
$\rho_{\lambda,1}$ is the reflectance at first wavelength ($\lambda 1$) and
$\rho_{\lambda,2}$ is the reflectance at second wavelength ($\lambda 2$)
In some embodiments $\rho_{\lambda,1}$ may represent an NIR reflectance and $\rho_{\lambda,2}$ represents a visible reflectance. In other embodiments $\rho_{\lambda,1}$ and $\rho_{\lambda,2}$ may both be visible band reflectances or infrared reflectances. Another form of the above equation is shown below:

$$MCR2 = \frac{\rho_{\lambda 1} + \rho_{\lambda 2}}{\rho_{\lambda 1} - \rho_{\lambda 2}}, \lambda 1 > \lambda 2$$

where MCR2 is the moisture compensated reflectance,
$\rho_{\lambda,1}$ is the reflectance at first wavelength ($\lambda 1$) and
$\rho_{\lambda,2}$ is the reflectance at second wavelength ($\lambda 2$)
Yet another form of the above equation is shown below:

$$MRC3 = \frac{\alpha}{\rho_{\lambda 1} - \rho_{\lambda 2}}, \lambda 1 > \lambda 2$$

where MCR3 is the moisture compensated reflectance,
$\rho_{\lambda,1}$ is the reflectance at first wavelength ($\lambda 1$) and
$\rho_{\lambda,2}$ is the reflectance at second wavelength ($\lambda 2$)
$\alpha$ is a constant typically equal to 1.

The common feature of MCR1, MCR2, and MCR3 is the wavelength difference in the denominator of each equation that is utilized to normalize a reflectance or function of reflectances with respect to the slope of the soil characteristic. The variables MCR1, MCR2, and MCR3 can be used as arguments in functions that calibrate the output of the sensor in terms of soil organic matter. In some embodiments the sensor can auto calibrate itself in real-time. The calibration can be performed using a number of methods of which include descriptive statistics and a field's average organic matter content. This average organic matter measurement is typically performed by soil sampling service providers and is based on the average of 8 to 10 soil samples per 40 acre region. Other non real-time methods of calibrating the sensor involve comparing multiple soil samples with sensor measurements to create a linear regression model that relates sensor readings to organic matter. This model can then be loaded into the sensor in order to provide a calibrated output. Another non real-time method involves post calibrating GPS referenced sensor data using GIS software or other computational means and GPS referenced soil samples.

Data calculated by the sensor's processing component is communicated to an operator or system controller via input/output interface 48. When the invention is incorporated into a sprayer or mapping system having several sensors networked together, the I/O interface will most preferably be a networkable serial port such a as RS485 port or CAN 2.0b port.

One embodiment of the sensor uses one or more monochromatic LEDs with each having a different emission spectra and a single detector to receive reflected light from the soil. In this embodiment, each LED is modulated on and off independently with respect to each other and the reflectance from the soil is measured by the photodetector (or photodetector array) and synchronously demodulated. Various colored LEDs can be used to probe different portions of a soils reflectance curve in order to determine soil properties.

A variation of this embodiment uses laser diodes instead of LEDs and yet another variation utilizes cross polarized filters in front of the LEDs and photodetector(s) to reduce the effect of specular reflections.

A variation of the previous embodiment uses a white LED that emits many colors simultaneously and one or more spectrally filtered photodetectors. In this embodiment, the LED is modulated on and off and the reflectance from the soil is measured by a photodetector or photodetector array and synchronously demodulated. Various filters can be in front of the photodetector(s) to probe different portions of a soils reflectance curve in order to determine soil properties.

As one skilled in the art can see, there are numerous variations of the disclosed apparatus that can be built that would still be within the scope of this invention.

Applications of Use-Methods

Figure 5:
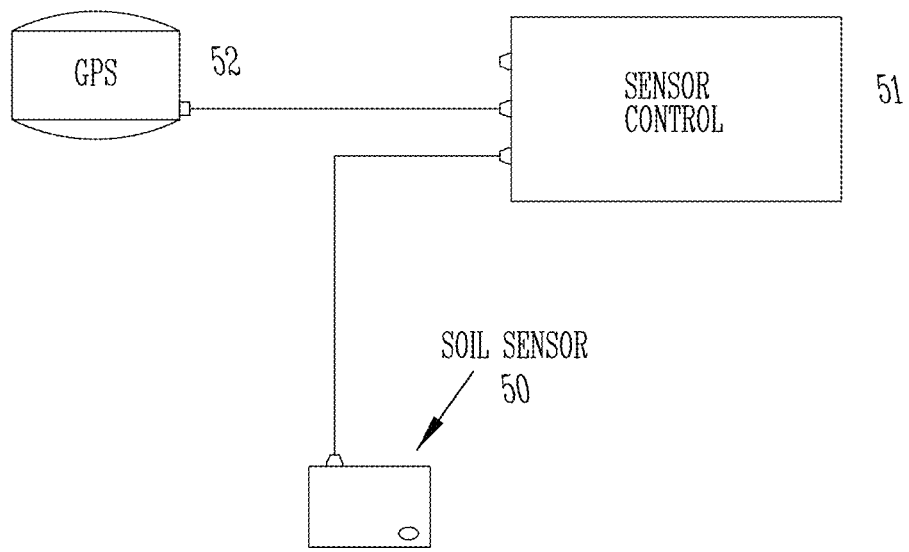
FIG. 5. Sensor utilized as component of mapping system.

FIG. 5 show a block diagram of the invention incorporated into a system that is used to map organic matter content variation within a field. Elements of the system include soil sensor 50, sensor controller 51, and GPS 52. The role of the sensor in this system is to measure the variations in organic matter content based on changes in sensed soil reflectance. Data produced by the sensor is collected by the system controller for storage and later analysis. Each sensor point is geo-referenced using the GPS connected the system controller. There are two primary ways in which mapping can be performed the system. First, the map collected by the system can be all inclusive, that is, every data point measured by the sensor can be stored away in the controller's memory for later retrieval and analysis. Second, the sensor/controller can be programmed with a defined set of rules so as to distinguish low organic matter regions of a landscape from high organic matter regions and vice versa and store only the regions of interest. This mode of operation, sometimes referred to as a scouting mode, saves storage space in the controller and reduces the amount of data processing that has to be performed.

Figure 6:
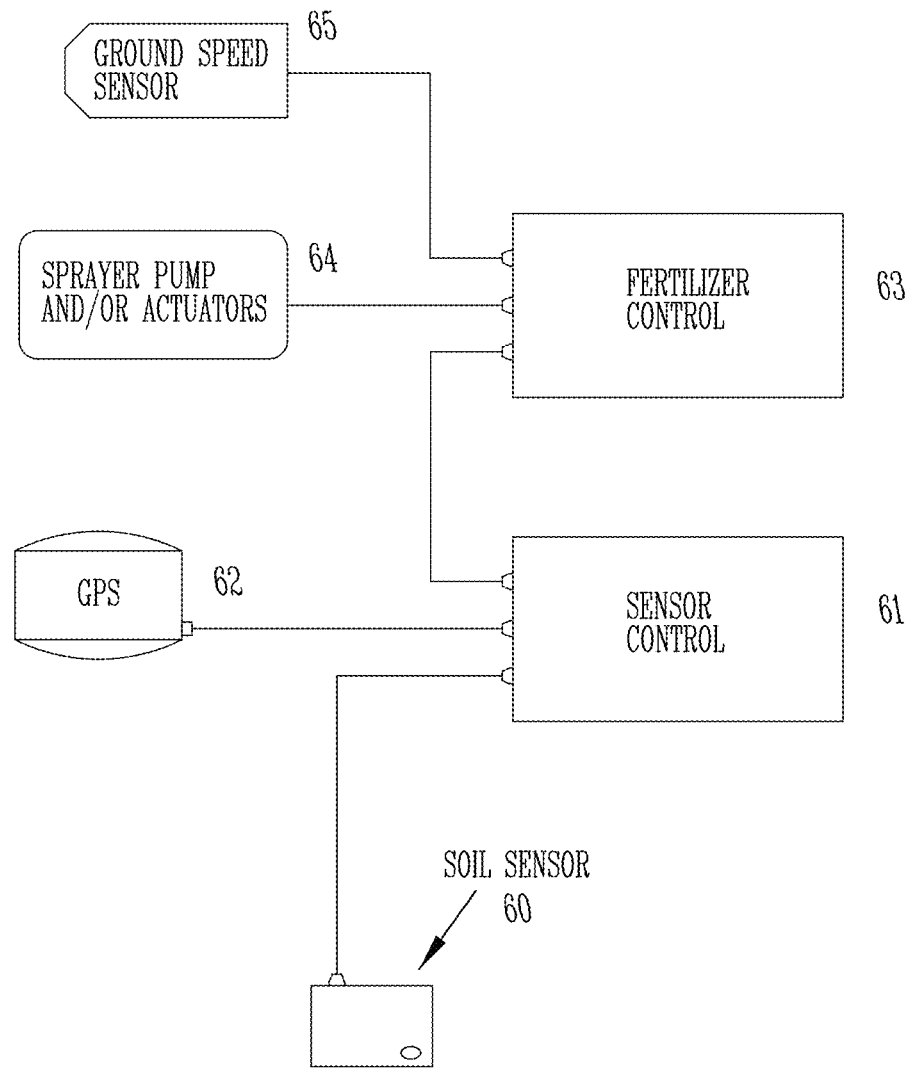
FIG. 6. Sensor utilized as component of variable rate and/or mapping system.

FIG. 6 show a block diagram of the invention incorporated into a system that is used for applying an agricultural product. Elements of the system include soil sensor 60, sensor controller 61, GPS 62, controller 63, sprayer pumps/seed actuators 64 and ground speed sensor 65. The agricultural product may be either in liquid or solid form and may be, but not limited to, a nutrient, mineral, seed, herbicide or fungicide or a combination of the aforementioned materials. GPS can be incorporated in the system when a map is required of soil variation (including organic matter) characteristics for later analysis. In addition to mapping soil characteristics, material dispensation rates can be mapped as well.

The benefits of a system such as the one just described are both economic and environmental. By using less fertilizer and only applying it where the crop needs it, the producer can lower his use of fertilizer and thus lower his production cost and by using less fertilizer and only applying it where the crop needs it based on organic matter content, reduced run-off and leaching into our watershed occurs. The organic matter content of the soil is an indicator of the amount of soil N available to the plant. The fertilizer rate that an applicator applies can be varied according to the sensor readings in real-time. Typically, soil organic matter contributes 10 to 30 kg/ha of soil N per percent of organic matter. A simple mathematical relationship that can be utilized by a variable fertilizer controller is shown below in the following equation, $$N_{APP} = N_{NOMINAL} - \alpha \cdot OM\ \%$$

where $N_{APP}$ is the fertilizer application rate varied by the controller, $N_{NOMINAL}$ is the flat fertilizer rate the producer would normally apply to the field, $\alpha$ is a coefficient that scales the applied fertilizer rate based on organic matter content and OM % is the organic matter content as determined or sensed by the disclosed apparatus.

Similarly, seeding rate can be modified based on organic matter content. Certain portions of a field do not yield as well as other portions due to the soil composition and in part this is indicated by the organic matter content of this region. As such, using a flat seeding rate across the field can result in lower returns because excess seed may be planted in portions of the field that do not have the fertility to support plant growth at high seed populations. In this case it is sometime desirable to decrease the seed rates in areas of the field that have low organic matter contents. A simple method to vary the seed rate of a planter is to use a threshold test as shown below:

$$S_{RATE} = \begin{Bmatrix} 20{,}000 & \text{if} & OM\ \% & < 1.2\% \\ 26{,}000 & \text{if} & OM\ \% & > 1.2\% \end{Bmatrix}$$

Where $S_{RATE}$ is the seed rate of the planter and

OM % is the organic matter content as determined or sensed by the disclosed apparatus.

In the above example, only a single threshold was utilized. Note however, multiple thresholds may be utilized to further optimize seed rate variation across an agricultural landscape.

Figure 9:
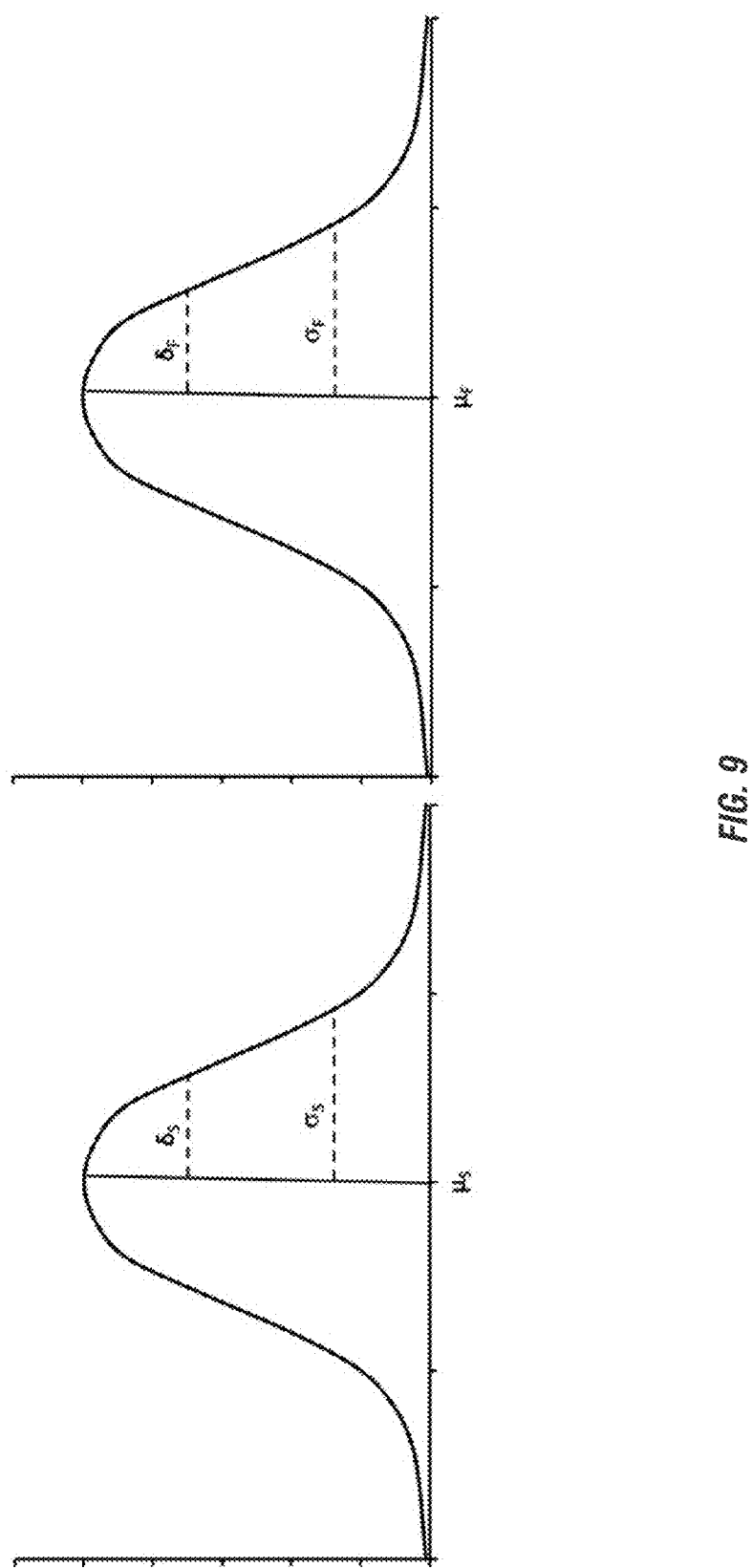
FIG. 9 illustrates data distributions of sampled sensor data and the true field parameter distribution.

The soil sensor data may be used in any number of ways. For example methodology may be used which rely on the statistical relationships between sampled sensor data and field parameter distributions. Normally the distributions are not known at the time of agrochemical application. The sampled sensor data can take the form of crop, soil, topology or combinations of the aforementioned. Various sensing technologies may be utilized to gather this data in real-time such as active crop canopy sensors, conductivity sensors, electrochemical sensors, soil color sensors, or other types of sensors or combinations of sensors. It is assumed that general shape of the physical field parameter distribution (spatial variation) is similar and relative to the sampled sensor distribution, see FIG. 9. The sampled sensor distribution can be created for real-time analysis by utilizing histograms or running sums statistics. The data populations for each distribution are related approximately using each distribution's coefficient of variation.

Figure 10A:
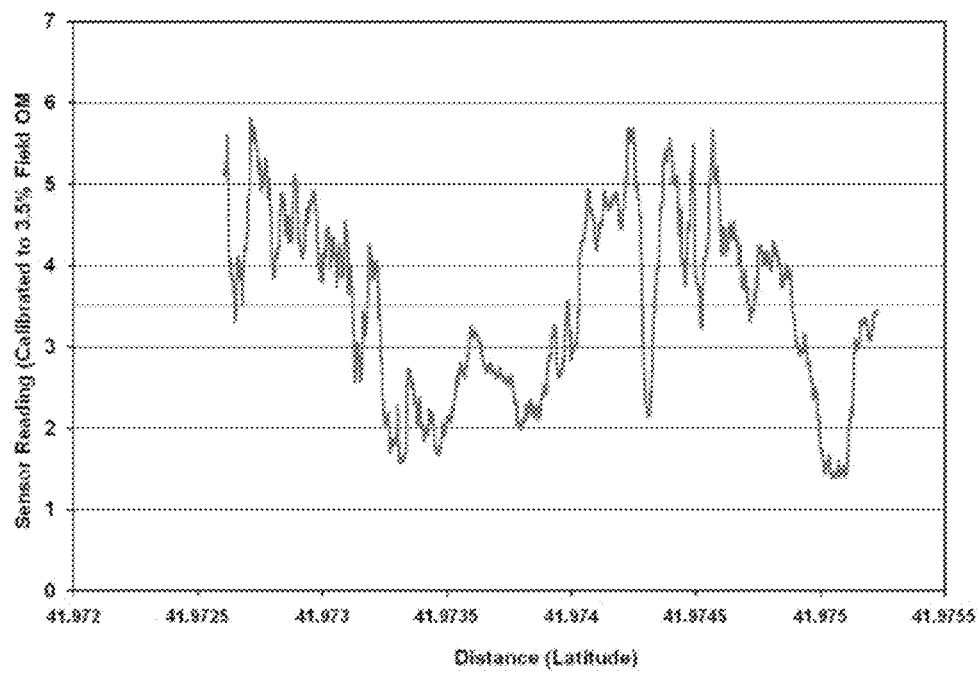
FIGS. 10A-10E illustrates sensed and sampled field transect.
Figure 10B:
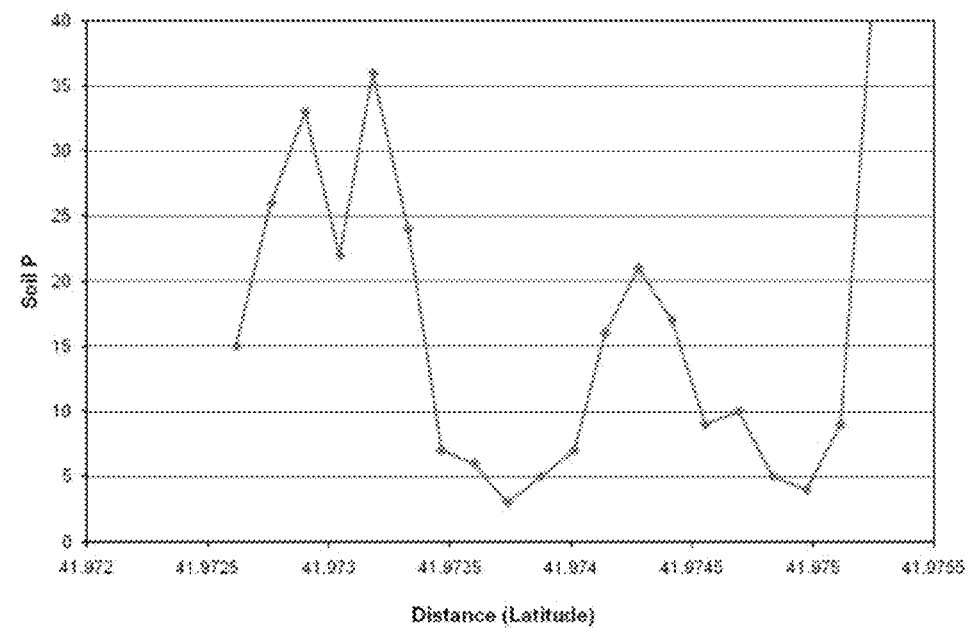
Figure 10C:
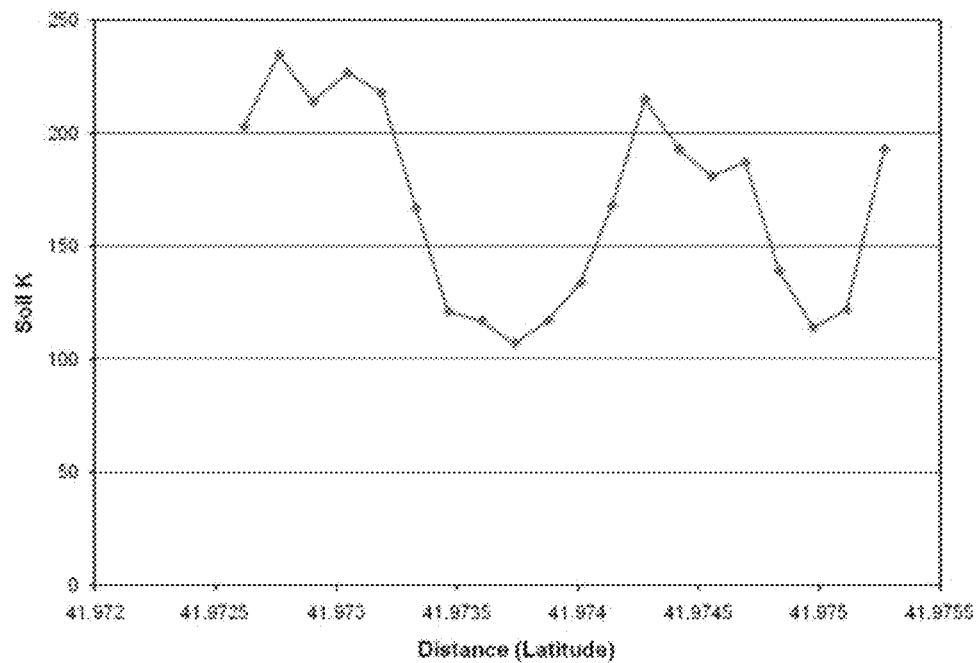
Figure 10D:
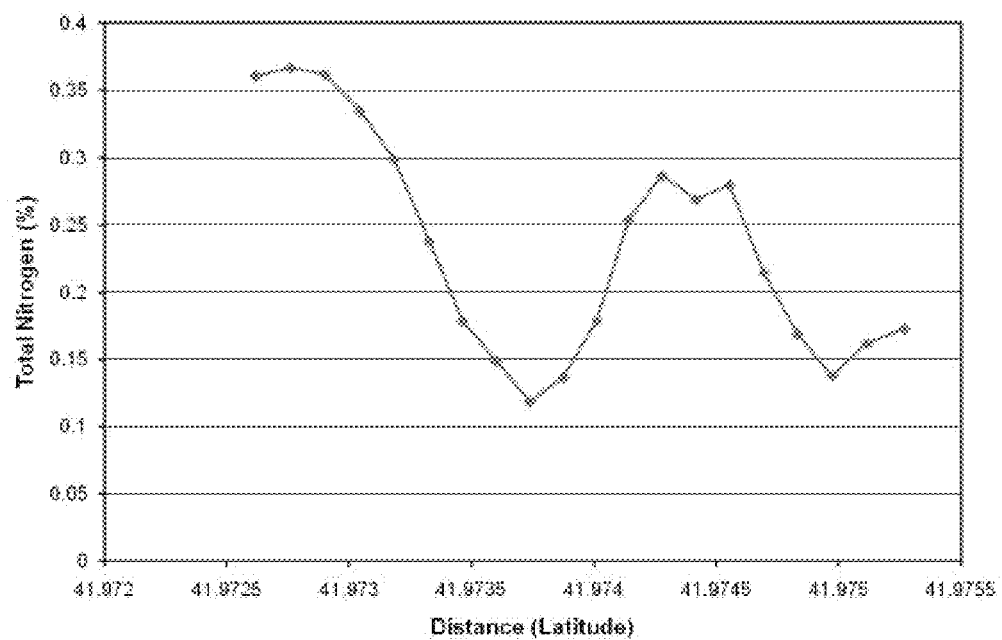
Figure 10E:
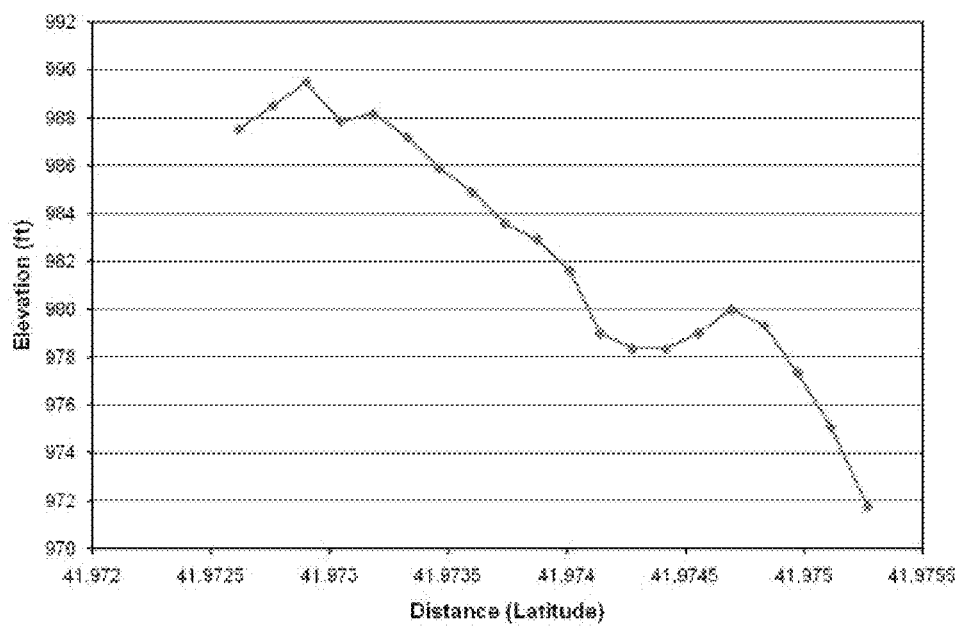
Figure 11:
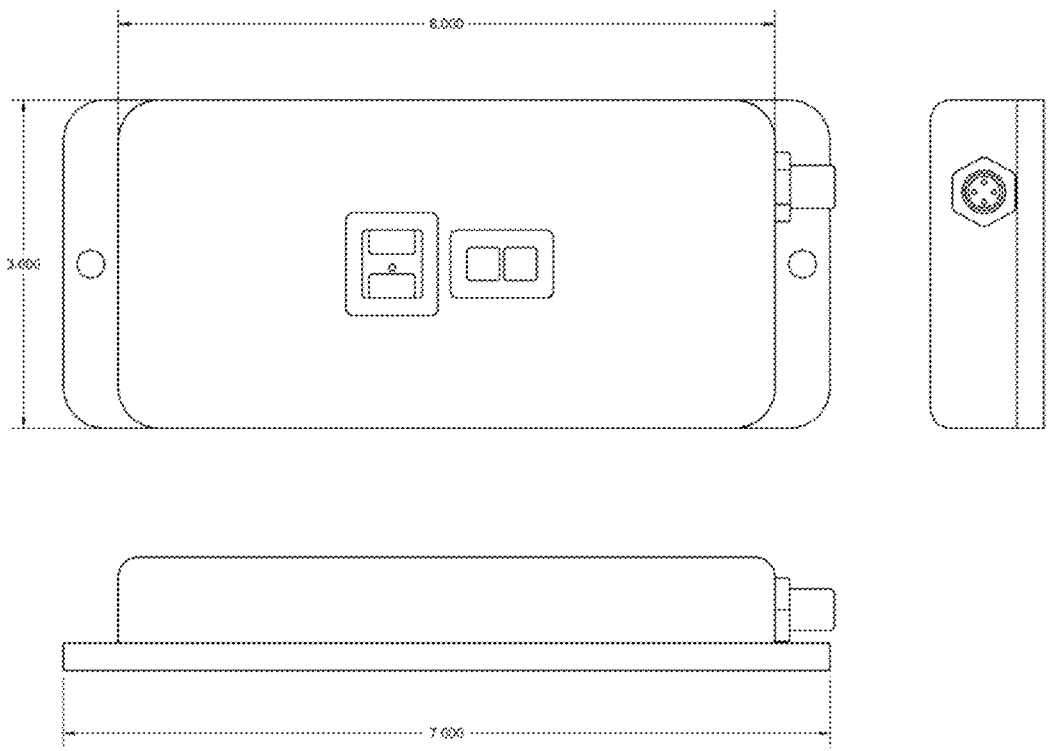
FIG. 11 illustrates one embodiment of a non-contact soil sensor. The instrument uses 2 wavebands; the spectral separation between the wavebands is typically greater than 200 nm.

Consider for example a soil color sensor such as the device depicted in FIG. 11. This particular soil sensing device can mount to a tractor, plow, planter or other agricultural implement or other type of vehicle. The sensor is capable of optically measuring variation in soil color while it is positioned above the soil. Other types of soil color sensors can be mounted in situ to measure the soil color under the soil surface. The sensor can measure soil color while in motion or when it is stationary. FIG. 10A shows sensor measurements obtained from the sensor across a typical field transect. FIG. 10B to FIG. 10E show manually sampled data along the soil transect measured by the sensor. As can be observed in FIG. 10A to FIG. 10E, hand sampled soil data have similar trends comparatively to the data produced by the sensor. The coefficient of variation (CV) for the sensor data distribution is:

$$CV_S = \frac{b \cdot m \cdot \sigma_S}{\mu_S}$$

where b is the correlation trend scalar {b=−1 for negative correlations; b=1 for positive correlations}, m is the regression scalar.

$\sigma_S$ is the standard deviation for the sensor data, and $\mu_S$ is the sensor mean data value.

Furthermore, the data from each distribution is also related by the following:

$$\frac{\delta_S}{\sigma_S} = \frac{\delta_F}{\sigma_F}$$

$\delta_S = x_S - \mu_S$ and $\delta_F = x_F - \mu_F$.

where the $\delta_S$ and $\delta_F$ are defined as

In the case of a soil sensor, the unknown variable $x_S$ for the sensor distribution might be defined for soil reflectance data as:

$$x_S = \frac{1}{\rho_{\lambda 2} - \rho_{\lambda 1}}$$

however, variable $x_S$ may take on other mathematical forms for other types of sensors. For example, $x_S$ might be a(n) Normalized Difference Vegetation Index (NDVI), spectral reflectance or other vegetation index when using a crop sensor.

If we assume that the distributions are related and can be related via the CVs of each distribution then $CV_S \cong CV_F$ which yields the following when the standard deviation and means are substituted in for the CV for each data distribution:

$$\frac{b \cdot m \cdot \sigma_S}{\mu_S} = \frac{\sigma_F}{\mu_F}$$

where b is a correlation scalar (b=1 if positive correlation or b=−1 if negative correlation)

and m is an intercept scalar (typically m is equal to 1).

Solving for the standard deviation of the filed in terms of sensor data results in:

$$\frac{\sigma_F}{\mu_F} = \frac{b \cdot m \cdot \sigma_S}{\mu_S} \Rightarrow \sigma_F = \frac{b \cdot m \cdot \sigma_S \cdot \mu_F}{\mu_S}$$

In the case of a soil sensor the field organic matter (OM) value is defined as the mean plus a delta to a point on the OM distribution curve. This can be parameterized in terms of sensor data via the synthesis:

$$OM = \mu_F + \delta_F$$
$$= \mu_F + \frac{\delta_S \cdot \sigma_F}{\sigma_S}$$
$$= \mu_F + \frac{\mu_F \cdot \delta_S \cdot b \cdot m}{\mu_S}$$
$$= \mu_F \left(1 + \frac{b \cdot m \cdot (x - \mu_S)}{\mu_S}\right)$$

The above relation can be utilized in various types of agrichemical or material application. One use might be for varying seed rate across a field based on relative organic matter distribution in a field. Another use maybe for varying herbicide application. Yet another application uses the OM term for soil fertilizer recommendations. This use is shown in the two following methods:

Method 1) N application method based on applying relative to the maximum rate:

$$N_{APP} = N_{REC} - g \cdot OM$$

where $N_{REC}$ is the recommended rate, OM is the soil organic matter, and g is the fertilizer sensitivity constant per percent of soil organic matter (g is typical 20 to 30 lbs N per percent of organic matter).

Method 2) N application method based applying around an average rate:

$$N_{APP} = N_{AVG} + g \cdot (\mu_F - OM)$$

where $N_{AVG}$ is the recommended average rate,

OM is the soil organic matter content, $\mu_F$ is the average field organic matter value (soil sampled via service provider), and g is the fertilizer sensitivity constant per percent of soil organic matter (g is typical 20 to 30 lbs N per percent of organic matter).

It should be noted that the above use of the field's average organic matter term is a proxy value in place of an actual sensor calibration. Using field or regional data can be useful in lieu of actual system calibration and can give agrochemical application systems considerable flexibility over a wide range of agricultural landscapes. The use of regional data enables the system to integrate years of agronomic science for immediate use circumventing years of costly testing and evaluation. In some circumstances, the use of field calibration data is not required and agrochemical application can be performed solely on the data distribution and statistical characteristics of real-time collected data.

It is to be understood that where regional data is used, adjustments may still be made. For example, applied agronomy and crop consultants may adjust regional recommendations for a particular field or sub-region. These adjustments may be made on additional data available to the consultants from the field or sub-region or relating to the field or sub-region.

Figure 12:
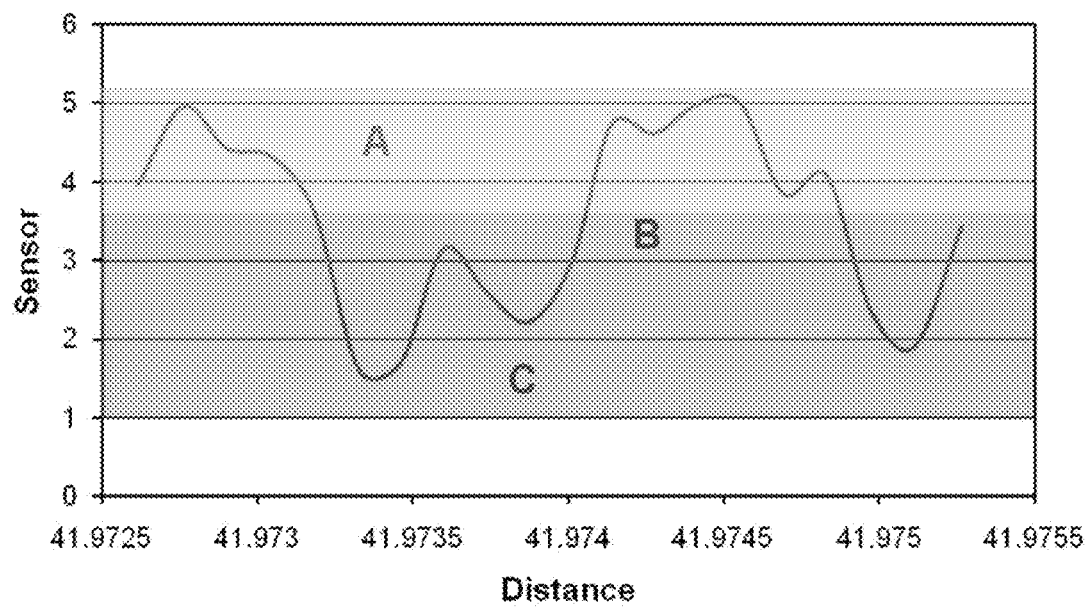
FIG. 12 illustrates sensor zone management. Each sensor zone depicted by zone labels A, B and C represents a unique region of the field. These regions can be differentially treated based on a user-defined (or system) rule set.

A useful embodiment pertains to the establishment of confidence limits to variably apply agrochemicals or other agricultural products like seeds to a field. Confidence limits for zones A, B and C as shown in FIG. 12 can be calculated in real-time using various statistical techniques. One method may include the use the sampled population's standard deviation. The boundary for the zone C may be calculated then from the following equation:

$$C_{Upper\ Limit} = \mu_S - n \times \sigma_S$$

where $C_{Upper\ Limit}$ is zone C's upper boundary,
$\mu_S$ is the mean of sampled sensor values,
n is a scalar and
$\sigma_S$ is the standard deviation of sampled sensor values.
Similarly, the lower boundary for zone A is calculated as follows:

$$A_{Lower\ Limit} = \mu_S - n \times \sigma_S$$

where $A_n$ is the normalized cumulative value determined over n bins,
N is the number of sample points contained in the histogram and
$h_i$ is the $i^{th}$ bin.

It follows then, by applying the sample percentages above, the limits for each zone can be determined using the following algorithm follows:

```
float zone_rate(*int hptr, float Cul, float All, float N, float sensor_data)
{
  int Ai, Ci;
  float Cthrsh, Athrsh;
//Variable initialization
        //hptr is a pointer to the histogram array h[n]
        //Cul is the upper limit for zone C
        //All is the lower limit for zone A
        //sensor_data is the most recent real-time data point
        Ci=1; //bin ptr for zone C upper limit
        Ai=1; // bin ptr for zone A lower limit
//Find bin pointer for zone C
        acc=0; // cumulative value
        While ((float)(acc)/N <Cul)
        {
                acc=acc+*(hptr+Ci); //accumulate values in histogram array h(i)
                Ci++;
        }
//Find bin pointer for zone A
        Ai=Ci;
        While ((float)(acc)/N <All)
        {
                acc=acc+*(hptr+Ai); //accumulate values in histogram array h(i)
                Ai++;
        }
        Cthrsh=dh*(float)(Ci--); //Calculate C zone threshold for comparing real-
                        time //data. Cthrsh is calculated by multiplying the bin ptr
                        Ci by the //bin width (dh).
        Athrsh=dh*(float)(Ai--); //Calculate B zone threshold for comparing real-
                        time //dat
    a. Athrsh is calculated by multiplying the bin ptr Ai by the bin width (dh).
    if (sensor_data<Cthrsh)
        return *zone_rate_C; //returns rate C pointed to by zone_rate_C ptr
    else if (sensor_data< Athrsh)
        return *zone_rate_B; //returns rate B pointed to by zone_rate_B ptr
    else
        return *zone_rate_A; //returns rate A pointed to by zone_rate_A ptr
}
``` where $A_{Lower\ Limit}$ is zone C's upper boundary,
$\mu_S$ is the mean of sampled sensor values
n is a scalar and
$\sigma_S$ is the standard deviation of sampled sensor values.
Zone B is defined then as:

$$B = A_{Lower\ Limit} - C_{Upper\ Limit}$$

Another method of calculating zone limits involves the use the sampled histogram. Assuming that the percentage of samples for each zone A, B, and C should be represented by 34%, 32% and 34% of the sampled data, the boundaries can be calculated by converting the ordinary histogram to a cumulative histogram searching for the boundaries using the established limits. A normalized cumulative histogram is defined by $$A_n = \frac{1}{N} \sum_{i=1}^{n} h_i$$

In either case, application rate values for A, B and C can be set by the producer or crop consultant and entered into the producer's VRA or planter system. For example, consider an N fertilizer application. The average application value (B zones) is determined to be 50 lbs N per acre. It is further established that A zones will be decreased 40% to 30 lbs N per acre and C zones increased 20% to 60 lbs N per acre. In operation, when the sensor provides a value that is in above the A zone threshold, the control system would apply the A zone rate. Likewise, the system would apply the B zone rate when the sensor value is greater than the C zone threshold and less than the A zone threshold. And finally, when the sensor value is below the C zone threshold, the C zone rate is applied by the control system.

This approach can be adapted for use on early season crop nutrient stress sensing as opposed to traditional means of determining nutrient stress relies on nutrient accumulation deficits, for example N, at later growth stages. For sensor based N application, N is applied to the crop at later growth stages because it is only then that the N stress can be detected and correlated using traditional sensor calibration and algorithmic techniques. The standard method to calibrate the sensors is to establish a high N reference strip or high N region in a field. At the time of in-season N application, the producer will drive over this region in order to capture sensor measurements for this crop. Ideally, these measurements represent crops that are growing in non N limiting conditions. The remainder of the field is compared to these measurements. Through the use of an algorithm or application table of values, new sensor readings are compared to the reference values and N is applied in accordance to the algorithm or position in the application table. This method will work for corn at growth stages between V7 and V14 but will not work for early growth stages of V2 to V6 because N is not a limiting factor for the plants growth. At early growth stages, other factors will affect the growth and will cause variation in collected sensor measurements. It is these factors (soil type, soil temperature, soil organic matter, field landscape and topology, drainage, etc.) that will not only affect the growth at an early development stage but will impact the plant's growth at later growth stages, that is, it is these influences that will cause a need for N application at later growth stages. Another limitation for some producers with respect to applying in-season N fertilizer is that the timing window for application is too narrow. Climate factors (heavy precipitation) may prevent the producer from entering his fields and applying N fertilizer at the proper time. Other producers are limited to early in-season application due to the fact they may not have access to or own high clearance application rigs that can enter their fields at later growth stages when the crop, typically corn, is very tall. As such, being able to apply N to the crops at an early growth stage V2 to V6 would be advantageous because it would extend the application window and allow producers with pull-type or drawn fertilizer equipment to access the fields when the crop stand is shorter. It should be noted, that this new application technique could also be used at later growth stages or with the traditional producer-created high N reference strip. Current methods of determining the optimum calibration value within a reference strip have had varied amounts of success. Use of this methodology of the present invention provides a robust and deterministic way to extract the calibration value from high reference regions or strips in a field at later growth stages when using optical crop sensing technology.

Figure 18:
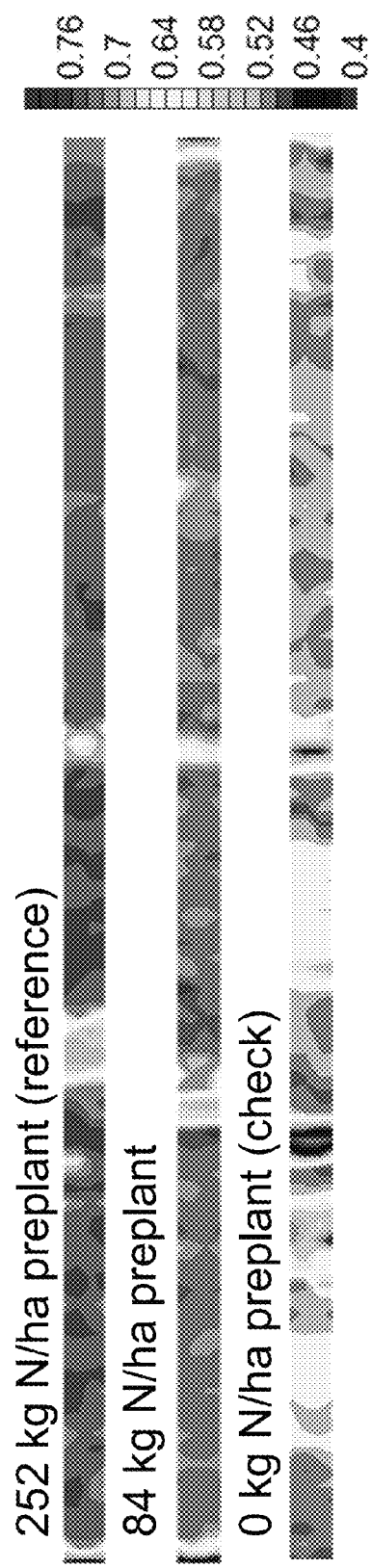
FIG. 18 illustrates amber NDVI values from active crop canopy sensor on at V10 growth stage for three adjacent 12-row corn strips receiving 0, 84, or 252 kg N/ha shortly before planting.

Another use for the invention pertains to scanning a traditional high N reference strip. FIG. 18 shows scans of field strips with 0, 84 and 252 kg N/ha of applied N. The 252 kg N/ha strip is a traditional high N reference strip. Note the variability along the length of this reference strip. In theory, this strip would be uniform and would represent the N sufficient portion of the field in which to calibrate the sensing system but in reality, though, this is not the case particularly when the field has received excessive amounts of rain fall. When precipitation is high, N leaches or runs-off the field and when precipitation is excessive, denitrification can occur and the N in the soil can volatize. In any case, the reference strip or region becomes increasingly non uniform. Many sensor calibration approaches, when using the traditional high N reference strip, involve scanning the reference strip to measure the strip's average vegetation index value or to measure a region (or portion of the strip) that has a high peak value for a certain length of time, for example, 3 to 4 seconds. These approaches will result in creating a calibration point that is under the optimal calibration point particularly when the reference strip has been damaged due to excessive precipitation. The invention as disclosed allows the user to create more robust calibration data via the real time statistical analysis methods presented above via statistical analysis of the collected data distribution of the reference strip.

This embodiment makes use of the real-time collected data by analyzing the distribution for its mean and maximum values ($\xi$) or a point near the maximum but higher than the mean. Note, this data can be collected before the N application operation, for example, from a previous trip through the field or from an aerial or satellite image and the data processed and saved as an N application map for spray applicator equipped with variable rate application system. The maximum point can be computed through the use of a cumulative histogram to find a particular limit value, for example the 95 percentile point, or some fractional multiple of the standard deviation, n·σ where n can typically vary from 0 to 3. After the maximum bound is determined, the minimum bound ($\eta$) it determined by subtracting the difference between the maximum and the mean from the mean or, $2 \cdot \mu - \xi$. Therefore, the agrochemical application equation is as follows:

$$N_{APP} = \begin{vmatrix} \text{if } x < \mu, \text{ then } N_{AVG} - \frac{N_{RECA} x(x - \mu)}{|\mu - \eta|} \\ \text{if } x > \mu, \text{ then } N_{AVG} - \frac{N_{RECB} x(x - \mu)}{|\mu - \xi|} \end{vmatrix}$$

where $N_{APP}$ is the applied N rate,
x is the current real-time sensor value,
$\mu$ is the average of sensor values,
$\eta$ is the lower bound of sensor values,
$\xi$ is the upper bound of sensor values,
$N_{AVG}$ is the recommended regional average application rate,
$N_{RECA}$ is N rate to apply in excess to the average rate down to bound $\eta$ and
$N_{RECB}$ is N rate to remove from the average rate up to bound $\xi$.

Figure 13:
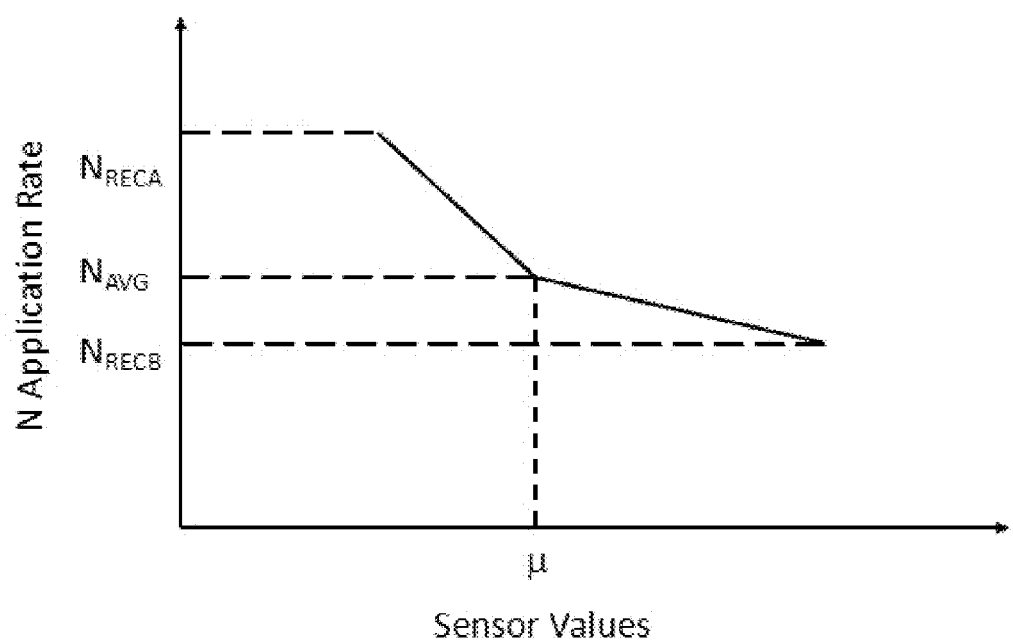
FIG. 13 illustrates early season N application method. The applied N rate is decreased for sensor values greater than μ and increased for sensor values greater than μ.

In the equation above, suppose that $N_{AVG}=80$, $N_{RECA}=70$, $N_{RECB}=50$. The response curve for this situation with a mean sensor value $\mu$ is shown in FIG. 13. Here we see that the applied N rate increases (applying more N to N deficient plants) as the real-time sensor value x tends toward the lower bound and decreases applied N (applying less N to N sufficient plants) as the real-time sensor value tends toward the upper bound. Note, the application trends can be reversed or the trends can be set to move in the same direction. The above example uses simple linear relationships; however, more sophisticated functionalities can be implemented instead. Furthermore, a dead zone can be established around the mean to apply only the average rate. When the sensor values extend past this bound, N can be varied according to the equation above or other function or rule set.

Another method for determining early season nutrient needs for corn (V2-V7) and other crops also uses a sampled data distribution in conjunction with an N application equation (or algorithm) such as the following N fertilizer application equation developed by Holland and Schepers (2010):

$$N_{APP} = (N_{OPT} - N_{PreFert} - N_{OM}) \cdot \sqrt{\frac{(1 - SI)}{\Delta SI \cdot (1 + 0.1 \cdot e^{m \cdot (SI_{Threshold} - SI)})}}$$

where, $N_{OPT}$ is the EONR or the maximum N rate prescribed by producers, $N_{PreFert}$ is the sum of fertilizer N applied prior to crop sensing and/or in-season N application, $N_{\overline{OM}}$ is the N credit for the field's average organic matter content, SI is the sufficiency index, ΔSI is the sufficiency index difference parameter, m is the back-off rate variable (0<m<100) and $SI_{Threshold}$ is the back-off cut-on point.

Figure 14:
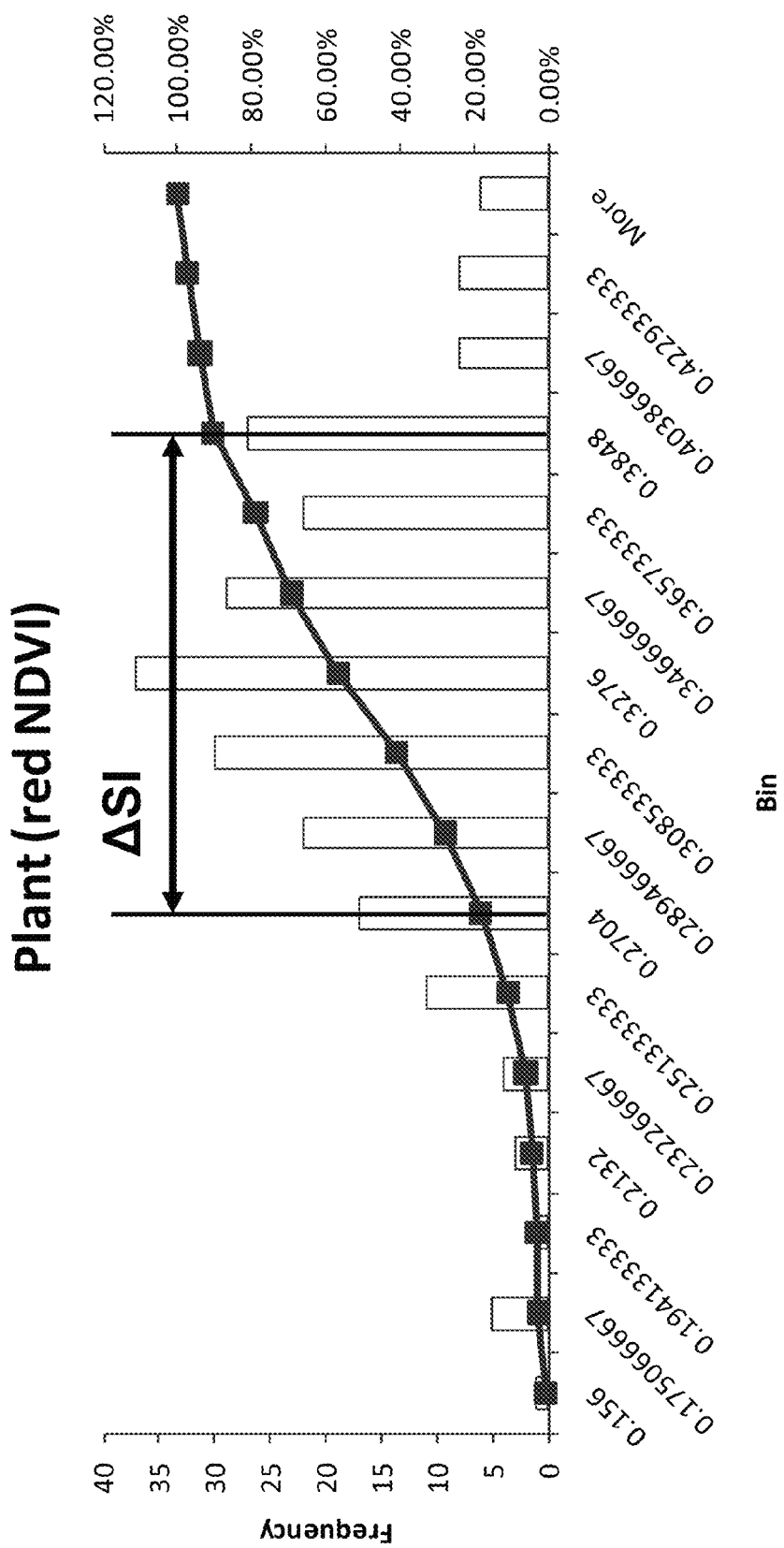
FIG. 14 illustrates sampled distribution of V3 corn (Mexico). Upper and lower calibration points for ΔSI are illustrated on histogram.

To use the above N application model, the ΔSI parameter is determined explicitly from the sampled data. Note, sometimes the ΔSI term is known from previous data collection and can be hardcoded into the N application equation. The histogram of sampled data is analyzed to determine the upper and lower calibration points. The calibration points are shown graphically in FIG. 14. In FIG. 14, ΔSI is also denoted over the range of vegetation index values that is covered by the calibration. A cumulative histogram is utilized to search for these calibration points. A normalized cumulative histogram is defined by $$A_n = \frac{1}{N} \sum_{i=1}^{n} h_i$$

where $A_n$ is the normalized cumulative value determined over n bins,

N is the number of sample points contained in the histogram and $h_i$ is the $i^{th}$ bin.

Each calibration point is easily determined from real-time sensor data using either individual or composite cumulative histogram searches. The cumulative histograms to search for the lower and the upper calibration points are $$A_{lower} = \frac{1}{N} \sum_{i=1}^{n} h_i \text{ and } A_{upper} = \frac{1}{N} \sum_{i=1}^{m} h_i$$

The difference between N sufficient crops having an SI equal to 1 and the ratio of the calibration points represents the ΔSI value as shown in the equation below.

$$\Delta SI = 1 - \frac{A_{lower}}{A_{upper}} = 1 - \frac{\frac{1}{N}\sum_{i=1}^{n} h_i}{\frac{1}{N}\sum_{i=1}^{m} h_i} = 1 - \frac{\sum_{i=1}^{n} h_i}{\sum_{i=1}^{m} h_i}$$

For example, if it is determined that the lower calibration point represents 20% of the occurrences in the histogram and the upper calibration point represents 95% of the occurrences in the histogram, then ΔSI can be calculated as using the following composite histogram algorithm:

```
float find_deltaSI(*int hptr, float lcal, float hcal, float N)
{
    int acc, li, hi;
    float H, L;
//Variable initialization
        //hptr is a pointer to the histogram array h[n]
        //lcal is the lower calibration point (lcal has value 0.2 passed to it)
        //hcal is the upper calibration point (hcal has value 0.95 passed to it)
        //sensor_data is the most recent real-time data point
        li=1; //bin ptr for lower calibration point
        hi=1; // bin ptr for upper calibration
//Find bin pointer for lower calibration point
        acc=0; // cumulative value
        While ((float)(acc)/N < lcal)
        {
                acc=acc+*(hptr+li); //accumulate values in histogram array h(i)
                li++;
        }
//Find bin pointer upper calibration point
        hi=li;
        While ((float)(acc)/N <hcal)
        {
                acc=acc+*(hptr+hi); //accumulate values in histogram array h(i)
                hi++;
        }
        H=dh*(float)(hi--); //Calculate calibration value for computing deltaSI
                //from realtime data. H is calculated by multiplying the
                bin ptr   //hi by the bin width (dh) from realtime data.
        L=dh*(float)(li--); // Calculate calibration value for computing deltaSI from
                //realtime data. Ll is calculated by multiplying the bin ptr
                li by //the bin width (dh).
        return (1-L/H); //return delta SI to the calling procedure
}
```

A consequence of precision agriculture technologies using the embodiment disclosed above pertains to incorporating these methods into best management practices (BMP) for agricultural material usage, in particular, embedding knowledge-of-use into materials that may be managed by the VRT systems. For example, consider a variable rate seeding application that uses zone management practices (real-time or map based). It may be difficult for the producer to fully take advantage of the particular seed genetics if certain management practices (seed rate, planting time, optimal fertilizer quantities and type, etc.) are not implemented. In this case, the bag of seed might have a barcode or RFID tag that might contain the BMP information for the VRT system. This information can be readily scanned or entered into the VRT system to automatically configure the seeder to optimally vary planting depth, seed rate, fertilizer rates, etc. This concept can also be extended to agrochemical application as well. Information provided by the manufacturer and imprinted on the material's packaging (barcode or code constants), asset specific memory integrated circuit such as the iButton memory circuit manufactured by Maxim (Sunnyvale, Calif.) or RFID tag can be scanned or loaded manually into the VRT system enabling the producer to optimally use the agrochemical without the need to manually configure the system. The information provided by the codes on the packaging may be utilized by the system to set up optimal control VRT system parameters. The use of such a system may assist in reducing the burden on the producer to implement the agricultural product manufacturer's recommendations. Note, the default configurations as provided by the agricultural product's barcode or RFID can be user modified by changing the settings loaded into the VRT controller. The BMP information may also include proprietary information of a chemical or seed company where proprietary information is used to determine best management practices, the proprietary information may be hidden from a user of the system. Thus, the producer can benefit from the proprietary information without the chemical or seed company needing to disclose the proprietary information to the producer. Furthermore, BMP information can be supplied to the VRT system via database as either a file or an ECU (electronic control module). The module may connect directly to real-time sensors and to the VRT system (as a bridge module) via the VRT system's control bus or to the VRT system via the system's control bus or expansion port independent of the real-time sensor equipment. The control bus can be a CAN bus, serial bus, multi-drop bus, dedicated expansion port, Ethernet bus, etc. Some embodiments may be as simple as a database file containing the manufacturer's BMP's that is loaded into a central user console in the tractor cab. In this embodiment, a seed company or agrochemical company could supply to customers a module that contains region specific BMP's for their product in order to maximize said product's performance in a particular region. For example, seed rates for a corn hybrid (or other crop) could be modified depending on the customer's particular soil type or climate. This type of system could be useful in taking advantage of a seed company's germplasm having particularly advantageous genetics for a given region (water stress resistance, nitrogen use efficiency, etc.). Access to the BMP recommendation in the ECU module's database for a particular agricultural material can be determined in conjunction with the aforementioned methods or via internet or cellular interface hence making it transparent to the user. The ECU module can also incorporate various mathematical modules, decision aids and statistical methods to best use BMP information. The ECU can provide BMP information to the VRT system when used in conjunction with real-time sensing equipment or without such equipment.

Figure 15:
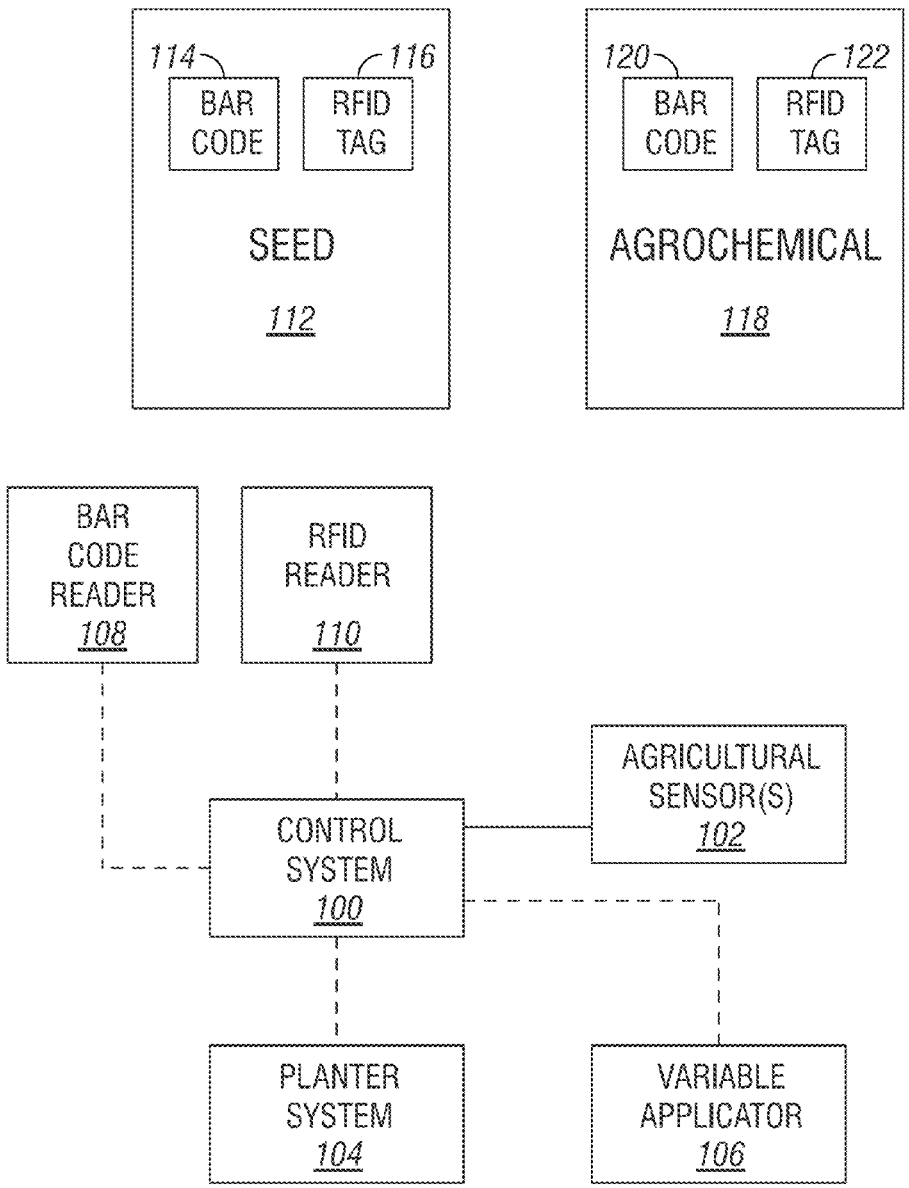
FIG. 15 illustrates one example of bar codes or tags on a bag which include information used in applying agrochemicals.

FIG. 15 illustrates an example where bar code or RFID information may be used. In FIG. 15, a control system 100 is shown which is operatively connected to one or more agricultural sensors 102. The control system 100 is also operatively connected to a system for applying agricultural products such as a planter system 104 or a variable applicator 106. The control system 100 is also in operative communication with a bar code reader 108 or RFID reader 110. A container such as a bag of seed 112 is shown which may include a bar code 114 and/or an RFID tag 116. The bar code is preferably a two-dimensional bar code. Similarly, a container of agrochemical 118 may also include a bar code 120 and/or an RFID tag 122. The bar codes may be read by the bar code reader 108 and information obtained therefrom may then be communicated to the control system 100 either manually or automatically. Similarly, the RFID tags may be read by the RFID reader 110 and information obtained therefrom may then be communicated to the control system 100. Information communicated may include best management practices information associated with the seed or agrochemical.

Figure 16:
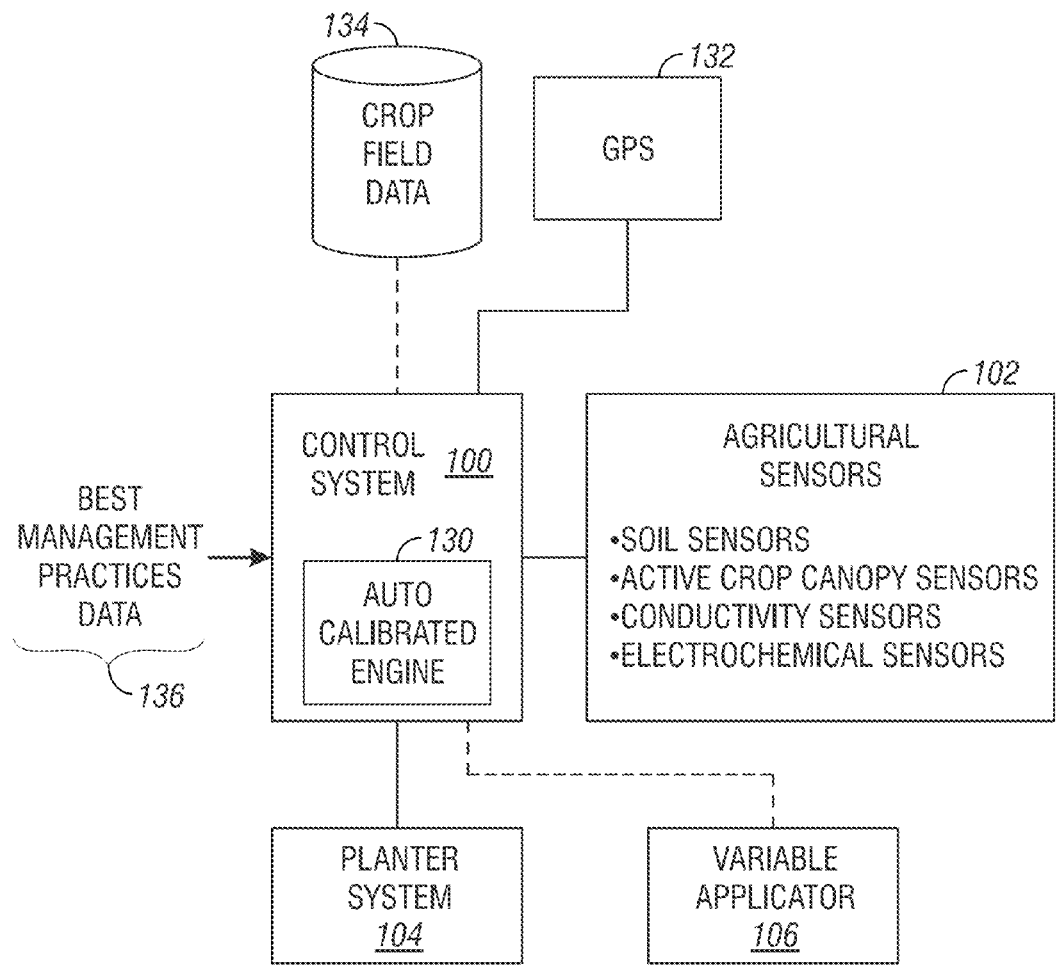
FIG. 16 illustrates another example of a system of the present invention.

FIG. 16 illustrates another example of the present invention. As shown in FIG. 16, the control system 100 is shown. The control system may include a microcontroller, microprocessor other type of intelligent control. The control system may be programmed or otherwise configured to perform the various methodologies described herein for determining the variable rates of application of agricultural products. Where the control system is programmed, instruction sets for performing various steps of the methodologies may be stored on a non-transitory computer readable storage medium or may be otherwise stored. The control system 100 may include an auto-calibration engine 130 as shown which uses histogram techniques or other statistical techniques to auto-calibrate values acquired by the agricultural sensors 102 to rates of application. In addition to this information, the control system 100 may also take into account best management practices data 136 associated with the agricultural products being used, the equipment being used, the field, or otherwise. In addition, the control system 100 can take into account crop/field data 134 which may include remote sensing data. A GPS 132 is shown which may be used to determine location which may be correlated with crop/field data 134 and/or best management practices data 136 and used by the control system 100.

Figure 17:
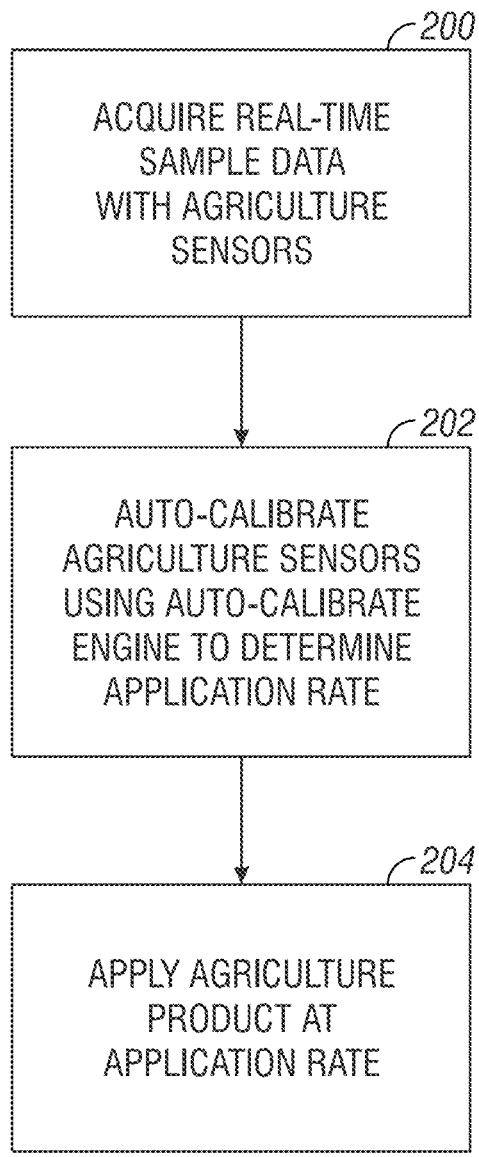
FIG. 17 illustrates another embodiment of a methodology of the present invention.

FIG. 17 illustrates an example of a methodology of the present invention. In step 200, real-time sampled data is acquired with agricultural sensors. In step 202 auto-calibration of the agricultural sensors is performed such as by using an auto-calibration engine to determine application rate. In step 204, agricultural products such as seed or agrochemicals are applied at the application rate. Thus, in this manner, the methodology allows for auto-calibration of the agricultural sensors.

Figure 19:
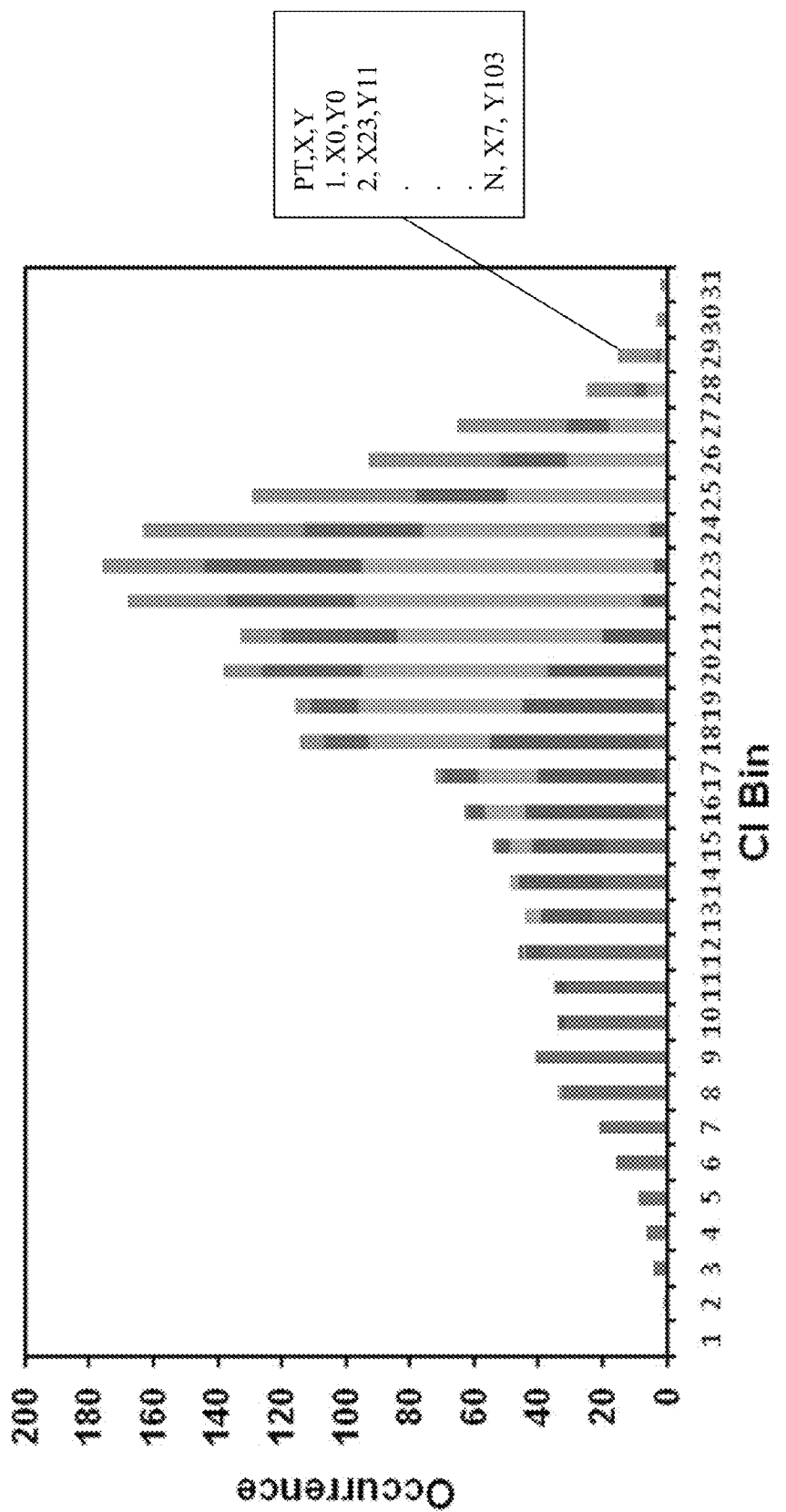
FIG. 19 illustrates an experiment study with 5 chemical treatments. Histogram bin 29 is opened to show sample points at spatial locations within experimental study plots. Positions for each bin can be scouted by technicians to collect soil, leaf tissue and seed samples.

Another application of the invention involves breeding and trait discovery for seed production. By tagging each data point in the collected histogram or data distribution with a physical location (x, y or even z for elevation) within the a seed producer/breeder's production plots, the location within the plots can be scouted after data collection to search out plants that are growing with exception vigor with respect to the experimental treatment. This is done simply by analyzing data within bin positions that exhibit a particular value of interest, see FIG. 19. In FIG. 19, bin 29 is opened to show spatial locations for plants having a particular characteristic, in this case the bin locations contain chlorophyll index (CI) values logged from a Crop Circle ACS 470 active crop sensor (Holland Scientific, Lincoln, Nebr.). Position can be determined using a GPS or other spatial or distance determination means. The treatment could be an imposed water, nutrient or chemical (herbicide for example) stress. The plants that perform the best may have certain expressed genetic traits that can be selected for use in a plant breeding program to create varieties of the plant that perform well under a particular stress.

Although various embodiments and examples have been described throughout, the present invention contemplates numerous variations and modifications. These include different types of agricultural products, different types of agricultural sensors, using different types of statistical methodologies to determine application values, using different types of data not sensed with the agricultural sensors such as remote sensing data, field or regional data, and best management practices data, and other data that may be available. The present invention is not to be limited to the specific examples and embodiments described.

REFERENCES

The following references are herein incorporated by reference in their entirety:

| U.S. Patent Documents | | |
|---|---|---|
| Re35100 | November 1995 | Monson et al. |
| 3,464,504 | September 1969 | Strange |
| 3,502,543 | March 1970 | Sewell |
| 3,593,809 | July 1971 | Derry |
| 4,266,878 | May 1981 | Auer |
| 4,284,150 | August 1981 | Davis |
| 4,332,301 | June 1982 | Jonell |
| 4,333,541 | June 1982 | Duty |
| 4,482,021 | November 1984 | Repski |
| 4,630,773 | December 1986 | Ortlip |
| 4,685,339 | August 1987 | Philipenko |
| 4,828,047 | May 1989 | Rogerson |
| 4,998,590 | March 1991 | Wells |
| 5,033,397 | July 1991 | Colburn, Jr. |
| 5,038,040 | August 1991 | Funk et al. |
| 5,044,756 | September 1991 | Gaultney et al. |
| 5,076,372 | December 1991 | Hellbusch |
| 526169 | May 1993 | Heller |
| 529869 | March 1994 | Huang et al. |
| 5,310,462 | May 1994 | Chen |
| 5,332,480 | July 1994 | Datta et al. |
| 5,355,815 | October 1994 | Monson |
| 5,366,601 | November 1994 | Jones et al. |
| 5,453,924 | September 1995 | Monson et al. |
| 5,461,229 | October 1995 | Sauter et al. |
| 5,467,271 | November 1995 | Abel et al. |
| 5,548,115 | August 1996 | Ballard |
| 5,561,516 | October 1996 | Noble et al. |
| 5,587,538 | December 1996 | Bratton |
| 5,887,491 | March 1999 | Monson et al. |
| 5,950,741 | September 1999 | Wright et al. |
| 601676 | January 2000 | Hale |
| 6,119,531 | September 2000 | Wendte et al. |
| 6,237,429 | May 2001 | Melnyk |
| 6,260,633 | July 2001 | Machek et al. |
| 6,360,829 | March 2002 | Naber et al. |
| 6,766,865 | July 2004 | Dagel et al. |
| 6,959,245 | October 2005 | Rooney et al. |
| 2005/0172733 | August 2005 | Drummond et al. |

OTHER REFERENCES

Barnes, E. M. and M. G. Baker. Multispectral Data for Mapping soil texture Possibilities and Limitations. Amer. Soc. Agric. Eng., 16(6), 731-741 (2000).

Bowers, S. A. and R. J. Hanks. Reflection of Radiant Energy from Soils. Soil Science. 100(2) 60-68 (1965).

Fernandez, R. N., D. G. Schultze, D. L. Coffin, and G. E. Scoyoc. Color, Organic Matter, and Pesticide Adsorption Relationships in a Soil Landscape. (July-August 1988), Soil Science of America Journal.

Griffis, C. L. "Electronic Sensing of Soil Organic Matter", Trans. Amer. Soc. Agric. Eng., 28:703-705 (1985).

Hoffer, R. M., "Biological and Physical Considerations in Applying Computer-Aided Analysis Techniques to Remote Sensor Data", Remote Sensing: The Quantitative Approach, Chapt. 5 (1978).

Hummel, J. W., K. A. Suddth and S. E. Hollinger. Soil moisture and organic matter prediction of surface and subsurface soils using NIR soil sensor. Computers and Electronics in Agriculture. 32, 185-193 (2001).

Krishman, P., B. J. Bulter, J. Hummel. Close-Range Sensing of Soil Organic Matter. Trans. Amer. Soc. Agric. Eng., 24:306-311 (1981).

Mangold, G., "New Tool Prescribes Precise Nitrogen Needs", Soybean Digest, p. 16b-16c (February 1988).

Shields, J. A., E. A. Paul, R. J. St. Arnaud and W. K. Head, "Spectrophotometric Measurement of Soil Color and Its Relationship to Moisture and Organic Matter", Can. J. Soil Sci., vol. 48, pp. 271-280 (1968).

Suddth, K. A. and J. W. Hummel. Portable Near Infrared Spectrophotometer for Rapid Soil Analysis. Amer. Soc. Agric. Eng., 36(1), 185-193 (1993).

Suddth, K. A. and J. W. Hummel. Geographic Operating Range Evaluation of a NIR Soil Sensor. Amer. Soc. Agric. Eng., 39(5), 1599-1604 (1995).

Tools with Eyes. Mid-March 1989. Farm Journal. pp. 16-18.

What is claimed is:

1. A method for application of an agricultural product to a field, the method comprising:
acquiring real-time sampled data using real-time agricultural sensors, wherein the real-time agricultural sensors include a soil sensor;
auto-calibrating the real-time agricultural sensors using statistical characteristics of the real-time sampled data to determine an application rate; and
applying the agricultural product to the field based on the application rate.

2. The method of claim 1 wherein the soil sensor includes a replaceable wear surface, a corrosion resistant enclosure, a light source for illuminating the soil with light, at least one photo detector configured to receive reflected light from the soil, and a scratch resistant optical window in contact with the soil, wherein the optical window allows light from the light source to illuminate the soil and the reflected light emanating from the soil to reach the at least one photo detector.

3. The method of claim 2 wherein the scratch resistant optical window has a mohs hardness greater than six.

4. The method of claim 2 wherein the light source comprises at least one light emitting diode.

5. The method of claim 2 wherein the light source comprises at least one laser diode.

6. The method of claim 1 further comprising determining a set of application rates wherein the application rate is within the set of the application rates and the step of auto-calibrating provides for selection of the application rate from the set of the application rates.

7. The method of claim 6 wherein the agricultural product comprises an agrochemical and the set of application rates are user-specified into a variable rate applicator.

8. The method of claim 6 wherein the agricultural product is seed and the set of application rates are user-specified into a planter system.

9. The method of claim 1 wherein the step of auto-calibrating is performed using information associated with packaging of seed or agrochemicals.

10. The method of claim 9 wherein the information associated with the packaging of seed or agrochemicals is encoded on one or more bar codes of the packaging.

11. The method of claim 9 wherein the information associated with the packaging of seed or agrochemicals is encoded in one or more radio frequency identification (RFID) tags of the packaging.

12. The method of claim 9 wherein the information associated with packaging of seed or agrochemicals comprises best management practices.

13. The method of claim 1 wherein the step of auto-calibrating the real-time agricultural sensors using the statistical characteristics of the real-time sampled data to determine the application rate comprises:
analyzing a distribution of the real-time sampled to determine a mean and a value proximate a maximum value;
calculating a minimum value from the mean and the value proximate the maximum value;
using the minimum value, the mean, and the value proximate the maximum value to determine the application rate.

14. The method of claim 1 wherein the step of auto-calibrating the real-time agricultural sensors using statistical characteristics uses a histogram method.

15. The method of claim 1 wherein the step of auto-calibrating the real-time agricultural sensors using statistical characteristics comprises using regional data.

16. The method of claim 1 wherein the step of auto-calibrating the real-time agricultural sensors using statistical characteristics comprises using field data.

17. An apparatus for application of an agricultural product to a field, the apparatus comprising:
a plurality of real-time agricultural sensors;
a control unit in operative communication with the plurality of real-time agricultural sensors, the control unit configured to perform steps of (a) acquiring real-time sampled data using the real-time agricultural sensors, (b) auto-calibrating the real-time agricultural sensors using statistical characteristics of the real-time sampled data to determine an application rate, and (c) applying the agricultural product to the field based on the application rate; and
wherein at least one of the plurality of real-time agricultural sensors is a soil sensor.

18. The apparatus of claim 17 wherein the soil sensor comprises (a) a replaceable wear surface, (b) a corrosion resistant enclosure, (c) a light source for illuminating the soil with light, (d) at least one photo detector to receive reflected light from the soil, and (e) a scratch resistant optical window in contact with the soil, wherein the optical window allows light from the light source to illuminate the soil and the reflected light emanating from the soil to reach the at least one photo detector.

19. The apparatus of claim 17 wherein the apparatus is further configured for determining a set of application rates wherein the application rate is within the set of the application rates and the step of auto-calibrating provides for selection of the application rate from the set of the application rates.

20. The apparatus of claim 17 wherein the agricultural product comprises an agrochemical and the set of application rates are user-specified into a variable rate applicator operatively connected to the control unit.

21. The apparatus of claim 17 wherein the agricultural product is seed and the set of application rates are user-specified into a planter system operatively connected to the control unit.

22. The apparatus of claim 17 wherein the step of auto-calibrating is performed using information associated with packaging of seed or agrochemicals.

23. The apparatus of claim 22 wherein the information associated with the packaging of seed or agrochemicals is encoded on one or more bar codes of the packaging.

24. The apparatus of claim 22 wherein the information associated with the packaging of seed or agrochemicals is encoded in one or more radio frequency identification (RFID) tags of the packaging.

25. The apparatus of claim 22 wherein the information associated with packaging of seed or agrochemicals further comprises best management practices information.

26. The apparatus of claim 17 wherein the step of auto-calibrating the real-time agricultural sensors using the statistical characteristics of the real-time sampled data to determine the application rate comprises:
analyzing a distribution of the real-time sampled to determine a mean and a value proximate a maximum value;
calculating a minimum value from the mean and the value proximate the maximum value;
using the minimum value, the mean, and the value proximate the maximum value to determine the application rate.

27. The apparatus of claim 17 wherein the step of auto-calibrating the real-time agricultural sensors using statistical characteristics uses a histogram method.

* * * * *